US011964003B2

(12) United States Patent
Cassavaugh et al.

(10) Patent No.: US 11,964,003 B2
(45) Date of Patent: Apr. 23, 2024

(54) STABLE SUSTAINED RELEASE THERAPEUTIC COMPOSITIONS IN APROTIC POLAR SOLVENTS AND METHODS OF MANUFACTURING THE SAME

(71) Applicant: XERIS PHARMACEUTICALS, INC., Chicago, IL (US)

(72) Inventors: Evan Cassavaugh, San Diego, CA (US); Steven Prestrelski, San Diego, CA (US)

(73) Assignee: XERIS PHARMACEUTICALS, INC., Chicago, IL (US)

( * ) Notice: Subject to any disclaimer, the term of this patent is extended or adjusted under 35 U.S.C. 154(b) by 77 days.

(21) Appl. No.: 17/359,202

(22) Filed: Jun. 25, 2021

(65) Prior Publication Data
US 2021/0401945 A1 Dec. 30, 2021

Related U.S. Application Data

(60) Provisional application No. 63/044,973, filed on Jun. 26, 2020.

(51) Int. Cl.
*A61K 38/26* (2006.01)
*A61K 47/02* (2006.01)
*A61K 47/20* (2006.01)
*A61K 47/34* (2017.01)

(52) U.S. Cl.
CPC .............. *A61K 38/26* (2013.01); *A61K 47/02* (2013.01); *A61K 47/20* (2013.01); *A61K 47/34* (2013.01)

(58) Field of Classification Search
None
See application file for complete search history.

(56) References Cited

U.S. PATENT DOCUMENTS

| | | |
|---|---|---|
| 4,727,041 A | 2/1988 | Aroonsakul |
| 5,065,747 A | 11/1991 | Bercu |
| 8,110,209 B2 | 2/2012 | Prestrelski et al. |
| 8,790,679 B2 | 7/2014 | Prestrelski et al. |
| 9,314,424 B2 | 4/2016 | Prestrelski et al. |
| 9,339,545 B2 | 5/2016 | Prestrelski et al. |
| 10,485,850 B2 | 11/2019 | Prestrelski et al. |
| 2007/0099835 A1* | 5/2007 | Qian ............... A61K 38/26 514/6.6 |

FOREIGN PATENT DOCUMENTS

| | | |
|---|---|---|
| WO | WO-2017053922 A1 | 3/2017 |
| WO | WO-2019014658 A1 | 1/2019 |

OTHER PUBLICATIONS

Korang-Yeboah et al. ("Effect of formulation and peptide folding on the fibrillar aggregation, gelation, and oxidation of a therapeutic peptide," Int. J. Pharmaceutics, 2021, 604, 120677, pp. 1-12) (Year: 2021).*
Boguszewsk, C. L., "Glucagon Stimulation Test: Has Its Time Come?," *Endocrine* 57(3):361-363, Humana Press, United States (Sep. 2017).
Cryer, P. E., "Mechanisms of Hypoglycemia-associated Autonomic Failure and Its Component Syndromes in Diabetes," *Diabetes* 54(12):3592-3601, American Diabetes Association, United States (Dec. 2005).
Dailymed, "Glucagon—glucagon injection, powder, lyophilized, for solution," NDC Code 63323-185-03, dailymed.nlm.nih.gov, accessible at URL:[https://dailymed.nlm.nih.gov/dailymed/drugInfo.cfm?setid=8c8acad6-44cc-43aa-966b-027e053be8f5] on Dec. 23, 2021, U.S. National Library of Medicine, United States, 17 pages (Apr. 2016).
Haymond, M., et al., "Nonaqueous, Mini-Dose Glucagon for Treatment of Mild Hypoglycemia in Adults With Type 1 Diabetes: A Dose-Seeking Study," *Diabetes Care* 39(3):466-468, American Diabetes Association, United States (2016).
International Search Report and Written Opinion for International Application No. PCT/US2021/039236, mailed on Oct. 11, 2021, European Patent Office, Netherlands, 12 pages.
Picazo, J., ed., "Glucagon in Gastroenterology," 113 pages, MTP Press Ltd., United Kingdom (1979).

(Continued)

*Primary Examiner* — Christina Bradley
(74) *Attorney, Agent, or Firm* — Sterne, Kessler, Goldstein & Fox P.L.L.C.

(57) ABSTRACT

The present invention relates to the use of aprotic polar solvents and an ionization stabilizing agent to prepare storage stable sustained release therapeutic formulations by dissolving a therapeutic agent (active ingredient) in an aprotic polar solvent system that can then be administered to patients suffering from or predisposed to a variety of physical conditions or disorders, notably hypoglycemia. In certain embodiments, the invention is directed to formulations comprising one or more therapeutic agents, as well as methods of making such formulations, comprising at least one therapeutic agent dissolved in an aprotic polar solvent such as DMSO, comprising at least one ionization stabilizing excipient (suitably, a mineral acid) and at least one sustained release modifier (suitably, a divalent cation-donating compound such as a zinc salt and/or a polymer such as a PLGA) in concentrations sufficient to impart physical and chemical stability to the therapeutic agent and to produce a formulation that results in a sustained release of the therapeutic agent into the bloodstream of an animal to which the formulation has been administered. The invention also relates to methods of producing such storage stable sustained release therapeutic formulations and to methods of treating, preventing and diagnosing certain physical conditions and disorders, notably hypoglycemia, by administering such storage stable sustained release therapeutic formulations to a patient.

47 Claims, 12 Drawing Sheets

(56) References Cited

OTHER PUBLICATIONS

Seaquist, E. R., et al., "Hypoglycemia and diabetes: a report of a workgroup of the American Diabetes Association and the Endocrine Society," *Diabetes Care 36*(5):1384-1395, American Diabetes Association, United States (May 2013).

Trading, F., et al., "Biological and chemical properties of two glucagon preparations with prolonged action," *European Journal of Pharmacology 7*(2):206-210, North-Holland Publishing Comp., Netherlands (1969).

Wilson, L. M. and Castle, J. R., "Stable Liquid Glucagon: Beyond Emergency Hypoglycemia Rescue," *Journal of Diabetes Science and Technology 12*(4):847-853, SAGE Journals, United States (Jul. 2018).

Yu, M., et al., "Battle of GLP-1 Delivery Technologies," *Advanced Drug Delivery Reviews 130*:113-130, Elsevier Science Publishers, Netherlands (May 2018).

Yuen, K. C., "Glucagon stimulation testing in assessing for adult growth hormone deficiency: current status and future perspectives," *ISRN Endocrinology 2011*:608056, 6 pages., International Scholarly Research Network, United States (2011).

\* cited by examiner

STABLE SUSTAINED RELEASE THERAPEUTIC COMPOSITIONS IN APROTIC POLAR SOLVENTS AND METHODS OF MANUFACTURING THE SAME

CROSS-REFERENCE TO RELATED APPLICATIONS AND INCORPORATION BY REFERENCE

The present application claims the benefit of U.S. Provisional Application No. 63/044,973, filed Jun. 26, 2020, the disclosure of which is incorporated herein by reference in its entirety.

BACKGROUND OF THE INVENTION

A. Field of the Invention

The present invention is in the field of medical and pharmaceutical arts. Certain embodiments relate generally to sustained release therapeutic aprotic solvent formulations with enhanced storage stability, comprising one or more active pharmaceutical ingredients that may be used as therapeutic formulations in treating, preventing, and/or diagnosing diseases, disorders and medical conditions in mammals, particularly humans. In particular, the invention concerns the use of aprotic polar solvents and at least one stabilizing agent to prepare stable sustained release therapeutic formulations by dissolving a therapeutic agent (active pharmaceutical ingredient), at least one ionization stabilizing agent, and at least one sustained release modifier, in an aprotic polar solvent system that can then be used with various devices for administration of the formulation. The invention also relates to methods of preparation and methods of use of such stable sustained release formulations.

B. Description of Related Art

Hypoglycemia, or low blood sugar, is a serious concern for people with diabetes. In healthy individuals, glucagon release is the body's primary defense against insulin-induced hypoglycemia. Glucagon counterbalances the action of insulin on glucose metabolism by stimulating glycogenolysis and gluconeogenesis, maintaining blood glucose within a normoglycemic range in healthy individuals.

As the primary counter-regulatory hormone to insulin, glucagon is used therapeutically as a first-line treatment of severe hypoglycemia in patients with diabetes. However, this use of glucagon has been limited by poor solubility and stability in water, leading to time-consuming reconstitution and preparation steps prior to administration to the hypoglycemic patient.

Gvoke® (glucagon injection) (Xeris Pharmaceuticals, Chicago, IL) is the first ready-to-use room-temperature, liquid, stable glucagon approved for the treatment of severe hypoglycemia in pediatric and adult patients with diabetes ages 2 years and above (1,2). This commercial, FDA-approved composition comprises glucagon at therapeutic levels in an aprotic polar solvent system (dimethylsulfoxide (DMSO)) and provides a storage stable immediate-release rescue formulation suitable for the treatment and prevention of severe hypoglycemia in patients suffering or predisposed thereto.

Parenteral formulations prepared in aprotic polar solvent systems (e.g. a DMSO-based solvent system), such as Gvoke (glucagon injection), benefit from improved drug molecule stability due to the absence of water-mediated degradation pathways. These pathways, including hydrolysis, deamidation and aspartic acid isomerization, are known to be largely responsible for peptide and protein instability in aqueous-based formulations. Furthermore, hydrolysis is also known to promote chemical instability with small molecule drugs. Prior research has demonstrated the improved stability of such formulations of other therapeutic peptides and small molecules relative to aqueous solutions comprising the same active pharmaceutical ingredients (see, e.g., U.S. Pat. Nos. 9,339,545 and 10,485,850, the disclosures of which are incorporated herein in their entireties).

The availability of liquid stable glucagon raises the potential for glucagon use beyond severe hypoglycemia rescue. In particular, a low-dose sustained release (SR) glucagon formulation may expand the treatment options available for indications such as hypoglycemia unawareness, nocturnal hypoglycemia, exercise-induced hypoglycemia, and congenital hyperinsulinism. For such conditions, patients often repeat the current treatment of oral carbohydrates several times in order to avoid a harrowing hypoglycemic event, potentially resulting in dramatic hyperglycemia. Treatment with a stable SR glucagon formulation may provide a more precise therapeutic option to prevent and treat hypoglycemia, avoiding the consumption of additional calories and the resulting hyperglycemia (see, e.g., Haymond, M. et al., *Diabetes Care* 39:466-468 (2016)), and would help to minimize any potential symptoms associated with glucagon levels above the therapeutic range (e.g., nausea, hyperglycemia). The development of stable SR formulations of other therapeutic peptides and small molecules may similarly provide more flexible options to patients suffering from or predisposed to a variety of other disorders and conditions suitably treated and/or prevented by administration of such formulations.

Thus, there remains a need for a formulation platform that couples the stability and solubility provided by aprotic polar solvent systems, while also providing the flexibility and enhanced physiological management provided by sustained release therapeutic formulations.

BRIEF SUMMARY OF THE INVENTION

Embodiments described herein provide storage stable sustained release (SR) compositions (formulations) comprising one or more therapeutically active ingredient (e.g., one or more active pharmaceutical ingredient), suitably a therapeutic peptide or small molecule. In other embodiments, the present invention provides methods of making such storage stable SR therapeutic formulations. In additional embodiments, the invention provides methods of using the storage stable SR formulations of the invention in methods of treating, preventing and/or diagnosing certain diseases, physical disorders or conditions in animals, including veterinary animals and humans, suffering from or predisposed to such diseases, physical disorders or conditions.

In certain exemplary embodiments, the present invention provides a storage stable SR glucagon formulation that is useful in treating and preventing hypoglycemia, particularly severe hypoglycemia, as well as being useful as an adjunct to certain diagnostic procedures. Such formulations suitable leverage the same nonaqueous formulation technology as an immediate release glucagon rescue product that is currently commercially available (Gvoke®; Xeris Pharmaceuticals, Chicago, IL) to address the stability and solubility challenges with aqueous glucagon. However, in the present invention a SR glucagon formulation is produced by further stabilizing the glucagon in solution with one or more cation-donating compounds, suitably a divalent zinc-containing compound such as a zinc salt, to reduce the aqueous solubility of glucagon while maintaining stability of the drug product. Such storage stable SR glucagon formulations of the present invention are clear, ready-to-use, non-aqueous solutions prior to injection. Upon subcutaneous administration, the zinc-stabilized glucagon forms a depot due to poor solubility under physiological conditions, promoting the gradual release of glucagon into the bloodstream.

Thus, in certain embodiments the present invention provides a sustained release therapeutic formulation comprising (a) at least one therapeutic agent, (b) at least one ionization stabilizing excipient, (c) at least one sustained release modifier, and (d) an aprotic polar solvent, particularly wherein the formulation is storage stable for at least six months at ambient temperature (e.g., 20° C.-25° C.), and wherein the formulation, when administered to a patient, results in the presence of therapeutic levels of the therapeutic agent in the blood of the patient for an extended period of time relative to an immediate release formulation comprising the same therapeutic agent. In certain such embodiments, the therapeutic agent is a peptide. Peptides suitably used in the storage stable SR formulations of the present invention include, but are not limited to, a glucagon peptide, glucagon analog, glucagon mimetic, or salt thereof. In other embodiments, the therapeutic agent is a small molecule, which may include any small molecule therapeutic, particularly those that are negatively charged at physiologic pH in humans and other animals. Examples of such small molecule therapeutics include but are not limited to levothyroxine, sumatriptan, ketorolac and ondansetron.

At least one ionization stabilizing excipient is dissolved in the aprotic solvent in an amount to stabilize the ionization of the therapeutic agent. In certain aspects the ionization stabilizing excipient is at a concentration of 0.01 mM to less than 200 mM. The ionization stabilizing excipient can be, but is not limited to, a mineral acid. In certain embodiments, the mineral acid can be selected from hydrochloric acid, sulfuric acid, nitric acid and phosphoric acid. The ionization stabilizing excipient may also be an organic acid (acids having a carboxylic acid —COOH functional group). Non-limiting examples of organic acids include acetic acid, citric acid, and amino acids. In certain aspects the aprotic solvent is DMSO. In particular aspects the ionization stabilizing excipient is a mineral acid and the aprotic solvent is DMSO In certain embodiments, the sustained release modifier is a divalent cation-donating compound, in particular a zinc-containing compound such as a zinc salt. Suitable zinc salts for use in such aspects of the invention include but are not limited to zinc acetate, zinc chloride and zinc sulfate.

In particular embodiments, the invention provides storage stable SR formulations wherein the therapeutic agent is glucagon, the ionization stabilizing excipient is a mineral acid, the sustained release modifier is a zinc salt and the aprotic solvent is DMSO.

In other embodiments, the invention provides methods of treating, ameliorating or preventing a disease, physical condition or disorder in a patient, such as a veterinary animal or a human, suffering from or predisposed to such disease, physical condition or disorder. Suitable such methods according to certain aspects of the invention comprise introducing an effective amount of a storage stable SR formulation of the invention into a patient in need thereof in a manner suitable to promote the sustained release of the therapeutic compound from the formulation into the bloodstream of the patient. In certain such embodiments, the formulation is introduced into the subject via parenteral administration, for example via injection (which may be a subcutaneous, intradermal or intramuscular injection) or infusion (which may be intravenous or which may be accomplished by pump infusion, e.g., by continuous or bolus pump infusion, or a combination thereof). In certain aspects, the invention provides methods of treating or preventing hypoglycemia in a human by administering to the human a storage stable SR glucagon formulation of the present invention.

In additional embodiments, the present invention provides methods of producing a storage stable sustained release therapeutic formulation, said method comprising mixing at least one ionization stabilizing excipient, at least one sustained release modifier, an aprotic polar solvent, and at least one therapeutic agent, thereby forming a storage stable therapeutic formulation that, when administered to a patient, results in the presence of therapeutic levels of said therapeutic agent in the blood of said patient for an extended period of time relative to an immediate release formulation comprising the same therapeutic agent. In suitable such aspects the therapeutic agent is a peptide, particularly a glucagon peptide, glucagon analog, glucagon mimetic, or salt thereof, the aprotic solvent is DMSO or deoxygenated DMSO, the ionization stabilizing excipient is a mineral acid, and the sustained release modifier a cation-containing compound, suitably a zinc-containing compound such as a zinc salt including but not limited to zinc sulfate, zinc chloride and zinc acetate.

In additional aspects, the invention provides methods of diagnosing a disease or physical disorder in a human patient by introducing an effective amount of one of the storage stable SR formulations of the invention into a patient suffering from or predisposed to, or suspected of suffering from or being predisposed to, a disease or disorder, as an adjunct to a diagnostic test and conducting the diagnostic test on the patient. Suitable formulations useful in accordance with this aspect of the invention include those described elsewhere herein, particularly storage stable SR glucagon formulations of the invention. Such diagnostic methods can be used for diagnosing a variety of diseases, physical disorders and physical conditions, including but not limited to Alzheimer's Disease, a growth hormone deficiency and a gastrointestinal disorder. In aspects where the methods are used in the diagnosis of a gastrointestinal disorder, the diagnostic test suitably is a radiology test of the gastrointestinal tract of said patient. In carrying out these diagnostic methods of the invention, the storage stable SR therapeutic formulation can be introduced into the patient by any parenteral route, particularly orally, intragastrically, intravenously, intramuscularly or intradermally.

To produce the storage stable SR therapeutic formulations of the invention, at least one ionization stabilizing excipient can be dissolved in the aprotic solvent in an amount sufficient to stabilize the ionization of the therapeutic agent. Suitable such ionization stabilizing excipients (including but not limited to mineral acids), and desirable concentrations for inclusion in the formulations of the invention, include those described hereinabove.

To produce the storage stable SR therapeutic formulations of the invention, at least one sustained release modifier can be dissolved in the aprotic solvent in an amount sufficient to prolong the kinetics of release of the therapeutic compound into the bloodstream of an animal, e.g., a veterinary animal or a human, relative to the release kinetics of immediate release formulations of the same therapeutic compound that do not contain a sustained release modifier, upon introduction of the formulations into the animal. In certain aspects the sustained release modifier is at a concentration of about 0.1 mM to about 100 mM, suitably about 0.5 mM to about 50 mM, and about 1 mM to about 25 mM. The sustained release modifier can be, but is not limited to, a divalent cation-donating compound, such as a divalent zinc-containing compound including but not limited to zinc sulfate, zinc chloride and zinc acetate. Particularly preferred in certain embodiments are zinc sulfate and zinc chloride. In particular aspects the sustained release modifier is a zinc salt such as zinc sulfate, zinc chloride or zinc acetate and the aprotic solvent is DMSO.

The formulations can further include a preservative at less than 10, 5, or 3% w/v. In certain aspects the preservative is benzyl alcohol.

The formulations can further include one or more disaccharides at less than 10, 5, or 3% w/v. In particular such aspects the disaccharide is trehalose dihydrate at about 5.5% w/v.

The formulations can further include one or more sugar alcohols at less than 10, 5 or 3% w/v. In particular such aspects the sugar alcohol is mannitol at about 2.9% (w/v).

In certain embodiments the formulation can have freezing point of about 10° C. or less, for example about 10° C., about 5° C., about 0° C., or less than about 0° C., e.g., less than −20° C., or between −50° C. to −70° C.

In certain embodiments the formulation comprises a therapeutic peptide or small molecule at a therapeutically effective amount. In particular such aspects the formulation comprises glucagon at a concentration (w/w) of about 0.5 mg/mL to about 20 mg/mL, suitably about 0.5 mg/mL, about 1 mg/mL, about 2 mg/mL, about 2.5 mg/mL, about 5 mg/mL, about 10 mg/mL, about 15 mg/mL, or about 20 mg/mL. In other aspects, the concentrations of zinc ion and glucagon are adjusted to provide a ratio of zinc:glucagon in the formulation of about 1:1 to about 20:1, and suitably a ratio of zinc:glucagon in the formulation of about 1:1, about 2:1, about 4:1, about 5:1, about 8:1, about 10:1, about 12:1, about 15:1, about 16:1 or about 20:1.

Certain embodiments are directed to methods of treating hypoglycemia by administering an effective amount of a formulation described herein to a subject in need thereof. In certain aspects the formulation is administered by infusion. In particular aspects the administration is by infusion via a pump which may be connected in series to an infusion set. The infusion can be a continuous and/or bolus pump infusion.

Certain embodiments are directed to methods of stably formulating a sustained release therapeutic agent. Exemplary such methods comprise mixing (a) at least one therapeutic agent, (b) at least one ionization stabilizing excipient, (c) at least one sustained release modifier, and (d) an aprotic solvent, resulting in a storage stable SR formulation of the therapeutic peptide or small molecule in a ready-to-use solution.

Without wishing to be bound by theory, it is thought that the sustained release modifier, in particular a divalent cation (e.g., a zinc-containing compound capable of donating Zn' ions), may form a coordination complex with one or more aspartic acid and/or histidine residues on peptide therapeutics resulting in the prevention of the formation of amyloid-like fibrils (a sign of instability of solutions of therapeutic peptides). It is theorized that the relatively low solubility of the zinc-peptide complex in water leads to sustained release of the peptide from the complex upon administration administration to an animal (such as a veterinary animal or a human), resulting in release of the peptide from the injection site into the bloodstream with more prolonged release kinetics than non-complexed (immediate release) peptide formulations (see, e.g., Trading, F. et al., *Eur. J. Pharmacol.* 7:206-210 (1969)). Thus, the formulation approaches described herein should be particularly useful in preparing storage stable SR formulations of a variety of aspartate- and/or histidine-containing therapeutic peptides, including but not limited to glucagon (and analogues thereof, GLP-1, GLP-2, adrenocorticotropic hormone (ACTH), leuprolide, hirudin, insulin, pramlintide, exendins, exenatide, gastric inhibitory peptide, calcitonin, calcitonin gene related peptide, amylin, adrenomedullin, angiotensin and the like. One of ordinary skill can readily determine other peptides containing one or more aspartic acid and/or histidine residues that may be suitably used in preparing the formulations of the invention.

Therapeutic molecules typically require an optimal or beneficial ionization profile in order to exhibit prolonged stability when solubilized in an aprotic polar solvent system. Maintaining the beneficial ionization profile of a therapeutic molecule dissolved in an aprotic polar solvent system can be achieved by using at least one ionization stabilizing excipient. In certain aspects the therapeutic molecule is not required to be previously dried from a buffered aqueous solution prior to reconstitution in the aprotic polar solvent system. The ability to use existing (e.g. commercially available) devices and the ability to circumvent the need for drying a therapeutic molecule (e.g., a peptide) from a buffered aqueous solution can save considerable time and cost throughout the various product development stages.

Stable solutions of a therapeutic agent(s) solubilized in non-aqueous aprotic polar solvents (e.g. DMSO) can be prepared by adding a specific amount of a compound, or combination of compounds, that function as an ionization stabilizing excipient. Without wishing to be bound by theory, it is believed that the ionization stabilizing excipient can act as a proton source (e.g., a molecule that can donate a proton to the therapeutic molecule) in the aprotic polar solvent system that may protonate the ionogenic groups on the therapeutic molecule such that the therapeutic molecule possesses an ionization profile having an improved physical and chemical stability in the aprotic polar solvent system. Alternatively, the ionization stabilizing excipient can act as a proton sink (e.g., a molecule or moiety that can accept/remove a proton from the therapeutic molecule) such that the therapeutic molecule possesses an ionization profile having an improved physical and chemical stability in the aprotic polar solvent system.

Certain embodiments are directed to a formulation comprising an ionization stabilizing excipient at a concentration of at least, at most, or about 0.01, 0.1, 0.5, 1, 10, or 50 mM to 10, 50, 75, 100, 500, 1000 mM, or up to the solubility limit of the ionization stabilizing excipient in the aprotic polar solvent system. In certain aspects the ionization stabilizing excipient concentration is between about 0.1 mM to about 100 mM, particularly about 1 mM to about 10 mM, e.g., about 1 mM, about 2 mM, about 3 mM, about 4 mM, about 5 mM, about 6 mM, about 7 mM, about 8 mM, about 9 mM, and about 10 mM. In certain embodiments the ionization stabilizing excipient may be a suitable mineral acid, such as hydrochloric acid, sulfuric acid, nitric acid and the like. In certain aspects the ionization stabilizing excipient may be an organic acid, such as an amino acid, amino acid derivative, or the salt of an amino acid or amino acid derivative (examples include glycine, trimethylglycine (betaine), glycine hydrochloride, and trimethylglycine (betaine) hydrochloride). In a further aspect the amino acid can be glycine or the amino acid derivative trimethylglycine. In certain aspects a peptide is less than 150, 100, 75, 50, or 25 amino acids. In further aspects the aprotic solvent system comprises DMSO. The aprotic solvent can be deoxygenated, e.g., deoxygenated DMSO. In certain embodiments, the formulation may be prepared by first adding the ionization stabilizing excipient to the aprotic polar solvent system, followed by addition of the therapeutic molecule. Alternatively, the therapeutic molecule may initially be solubilized in the aprotic polar solvent system followed by addition of the ionization stabilizing excipient. In a further aspect, the ionization stabilizing excipient and the therapeutic molecule may be solubilized simultaneously in the aprotic polar solvent system. In certain aspects the therapeutic agent is glucagon, a glucagon analogue, or salt thereof.

Other embodiments of the present invention are directed to methods of stably formulating a therapeutic agent (e.g., a peptide or a small molecule) comprising: (a) calculating or determining the appropriate ionization stabilizing excipient (e.g. proton concentration) needed to achieve a stabilizing ionization profile of a target therapeutic agent (e.g., a peptide(s) or small molecule(s)) in an aprotic polar solvent system; (b) mixing at least one ionization stabilizing excipient with the aprotic polar solvent system to attain an appropriate ionization environment that provides the ionization profile determined in (a); and (c) solubilizing the sustained release modifier(s) and the target therapeutic agent(s) in the aprotic solvent having an appropriate environment to physically and chemically stabilize the therapeutic agent. In certain non-limiting aspects the therapeutic agent is chemically or physically stable for at least or about 0.25, 0.5, 1, 2, 3, 4, or 5 years, and more preferably about 0.25 to about 2 years, at room temperature, at refrigerated temperatures (e.g., about 2° C. to about 10° C. or about 2° C., about 3° C., about 4° C., about 5° C., about 6° C., about 7° C., about 8° C., about 9° C. or about 10° C.), or at sub-zero temperatures (e.g., about –4° C. to about –80° C., or about –4° C., about –10° C., about –15° C., about –20° C., about –25° C., about –40° C., about –45° C., about –50° C., about –60° C., about –70° C., or about –80° C.). In certain aspects the dissolution of the therapeutic agent and the addition of the ionization stabilizing excipient and the sustained release modifier to the aprotic polar solvent system can be done in any order or concurrently, thus the ionization stabilizing excipient and the sustained release modifier can be mixed first followed by dissolution of the therapeutic agent, or the therapeutic agent can be dissolved first followed shortly thereafter (e.g., within about 5 minutes) by addition of the ionization stabilizing excipient and the sustained release modifier to the solution, or the ionization stabilizing excipient, the sustained release modifier and/or the therapeutic agent can be added or dissolved in an aprotic polar solvent system concurrently. In some embodiments, the addition of the ionization stabilizing excipient(s) may occur prior to addition of the therapeutic agent and/or the sustained release modifier to promote dissolution in the aprotic polar solvent system. One or more additional formulation components (e.g. preservatives, surfactants, polysaccharides, sugar alcohols, etc.) may be incorporated into the formulation either prior to or following addition of the therapeutic agent. In a further aspect the entire amount of a component (e.g., a therapeutic agent or an ionization stabilizing excipient) need not be mixed at a particular point; that is, a portion of the one or more components can be mixed first, second, or concurrently, and another portion mixed at another time, first, second, or concurrently. The concentration of the therapeutic agent and/or ionization stabilizing excipient added to the solution can be between 0.01, 0.1, 1, 10, 100, 1000 mM, or up to its solubility limit, including all values and ranges there between. In certain aspects the aprotic polar solvent system is deoxygenated. In a further aspect the aprotic polar solvent in the solvent system comprises, consists essentially of, or consists of DMSO or deoxygenated DMSO.

In a further aspect of the present invention there is disclosed a method for treating or preventing a condition, disease, disorder, etc. comprising administering to a subject in need thereof a formulation(s) of the present invention in an amount effective to treat or prevent the condition, disease, disorder, etc. Any suitable dosage of a therapeutic agent (e.g., protein, peptide, or small molecule) may be administered in the methods of the present invention. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. In certain aspects hypoglycemia can be treated by administering a formulation described herein comprising an effective amount of glucagon.

The stable SR formulations described herein are useful for the parenteral injection of any therapeutic agent (protein, peptide, and/or small molecule) that has limited or poor stability or solubility in an aqueous environment. In certain aspects a formulation as described herein is provided in as an injectable formulation. The injectable formulation can be administered into the epidermal, dermal, subcutaneous or intramuscular layer of a patient. In certain aspects the formulations are administered intracutaneously.

Thus, in some embodiments, the therapeutic agent or peptide or salt thereof is selected from the group consisting of glucagon, pramlintide, insulin, icatibant, leuprolide, an LHRH agonist, parathyroid hormone (PTH), adrenocorticotropic hormone (ACTH), hirudin, amylin, botulinum toxin, hematide, an amyloid peptide, cholecystokinin, a conotoxin, a gastric inhibitory peptide, an antibody (which may be monoclonal or polyclonal) or a fragment thereof, an immunogenic peptide (e.g., a peptide or peptide complex derived from a virus, a bacterium, or any prokaryotic or eukaryotic organism or cell thereof), an insulin-like growth factor, a growth hormone releasing factor, an anti-microbial factor, glatiramer, glucagon-like peptide-1 (GLP-1), a GLP-1 agonist, exenatide, analogs thereof, and mixtures thereof. In one embodiment, the peptide is glucagon or a glucagon analog or a glucagon peptidomimetic. In another embodiment, the peptide is parathyroid hormone. In another embodiment, the peptide is ACTH. In yet another embodiment, the peptide is leuprolide. In still another embodiment, the peptide is glatiramer. In yet another embodiment, the peptide is icatibant. In yet another embodiment, a first peptide is pramlintide and a second peptide is insulin. In still another embodiment, the first peptide is glucagon and the second peptide is exenatide. In other embodiments, the stable formulations used in accordance with the present invention comprise co-formulations or mixtures of the types of compounds described herein, such as at least one peptide, at least one small molecule, and combinations thereof.

Definitions

The term "container," "reservoir," "infusion set," "pump," "formulation-flow path," "fluid flow path," etc. should be interpreted as interchangeable and equivalent being these components will be in direct contact with the formulations being administered or stored with potential to interact with the components and their surfaces. The terms imply any and all components that the formulation will contact during storage (e.g., pump reservoir) and delivery (e.g., fluid flow path in pump and the infusion set when connected in series to a pump). The term "infusion set" as used herein may be interpreted to include both internal infusion sets (i.e., those contained within patch pumps) as well as complete tubing systems that connect a pump to the pump user and are generally external to the pump. In certain configurations, external infusion sets include a cannula (e.g. for subcutaneous administration), an adhesive mount, quick-disconnect, and a pump cartridge connector (for example, a Luer-type connector).

The terms "formulation" and "composition" may be used interchangeably herein, and as used herein refer to an admixture of at least two components to produce a preparation comprising all of those components, some of those components, or complexes or reaction mixtures or reaction resulting from the admixture of the components.

The term "dissolution" as used herein refers to a process by which a material(s) in a gas, solid, or liquid state becomes a solute(s), a dissolved component(s), of a solvent, forming a solution of the gas, liquid, or solid in the solvent. In certain aspects a therapeutic agent or an excipient, e.g., an ionization stabilizing excipient or sustained release modifier or other component, is present in an amount up to its solubility limited or is fully solubilized. The term "dissolve" refers to a gas, liquid, or solid becoming incorporated into a solvent to form a solution The term "elastomer" as used herein refers to a natural or synthetic polymer having elastic properties. The terms "elastomer" and "rubber" may be used interchangeably herein.

The term "excipient" as used herein refers to a natural or synthetic substance formulated alongside the active or therapeutic ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing or reducing aqueous or non-aqueous solubility, adjusting tonicity, mitigating injection site discomfort, depressing the freezing point, or enhancing stability. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

"Small molecule drugs" in the context of the present invention are biologically active compounds (and salts thereof) that can bring about a desired, beneficial, and/or pharmacological effect on a subject. These "small molecule drugs" are organic or inorganic compounds. Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

The term "therapeutic agent" or "therapeutic" encompasses proteins, peptides, small molecule drugs, and pharmaceutically acceptable salts thereof. Useful salts are known to those skilled in the art and include salts with inorganic acids, organic acids, inorganic bases, or organic bases.

Therapeutic agents useful in the present invention are those protein, peptide, and small molecule compounds that affect a desired, beneficial, and often pharmacological, effect upon administration to a human or an animal, whether alone or in combination with other pharmaceutical excipients or inert ingredients.

The term "peptide" and "peptide compound" refers to amino acid or amino acid-like (peptidomimetics) polymers of up to about 200 amino acid residues bound together by amide (CONH) or other linkages. In certain aspects a peptide can be up to 150, 100, 80, 60, 40, 20, or 10 amino acids. "Protein" and "protein compound" refer to polymers of greater than 200 amino acid residues bound together by amide linkages. Analogs, derivatives, agonists, antagonists, and pharmaceutically acceptable salts of any of the peptide or protein compounds disclosed here are included in these terms. The terms also include peptides, proteins, peptide compounds, and protein compounds that have D-amino acids, modified, derivatized, or naturally occurring amino acids in the D- or L-configuration and/or peptomimetic units as part of their structure.

"Analogue" and "analog," when referring to a peptide or protein, refers to a modified peptide or protein wherein one or more amino acid residues of the peptide or protein have been substituted by other amino acid residues, or wherein one or more amino acid residues have been deleted from the peptide or protein, or wherein one or more amino acid residues have been added to the peptide or protein, or any combination of such modifications. Such addition, deletion, or substitution of amino acid residues can take place at any point, or multiple points, along the primary structure comprising the peptide, including at the N-terminal of the peptide or protein and/or at the C-terminal of the peptide or protein.

"Derivative," in relation to a parent peptide or protein, refers to a chemically modified parent peptide or protein or an analog thereof, wherein at least one substituent is not present in the parent peptide or protein an analog thereof. One such non-limiting example is a parent peptide or protein which has been covalently modified. Typical modifications are amides, carbohydrates, alkyl groups, acyl groups, esters, pegylations and the like.

"Single-phase solution" refers to a solution prepared from a therapeutic agent that is dissolved in a solvent, or solvent system (e.g., mixture of two or more solvents (e.g. solvent and a co-solvent)), wherein the therapeutic agent is completely dissolved in the solvent or solvent system and there is no longer particulate matter visible, such that the solution can be described as optically clear. A single-phase solution may also be referred to as a "single-phase system," and is distinguished from a "two-phase system" in that the latter is comprised of particulate matter (e.g. powder) suspended in a fluid.

"Inhibiting" or "reducing" or any variation of these terms includes any measurable decrease or complete inhibition to achieve a desired result.

"Effective" or "treating" or "preventing" or any variation of these terms means adequate to accomplish a desired, expected, or intended result.

"Chemical stability," when referring to a therapeutic agent, refers to an acceptable percentage of degradation products produced by chemical pathways such as oxidation and/or hydrolysis and/or fragmentation and/or other chemical degradation pathways. In particular, a formulation of the type described herein may be considered chemically stable if no more than about 20% breakdown products are formed after at least one year of storage at the intended storage temperature of the product (e.g., refrigerated storage or subzero storage); or storage of the product at accelerated conditions (25° C./60% relative humidity) for one month, two months or preferable three months. In some embodiments, a chemically stable formulation has less than 30%, less than 25%, less than 20%, less than 15%, less than 10%, less than 5%, less than 4%, less than 3%, less than 2%, or less than 1% breakdown products formed after an extended period of storage at the intended storage temperature of the product.

"Physical stability," when referring to a therapeutic agent, refers to an acceptable percentage of aggregates (e.g., dimers, trimers and larger forms) being formed. In particular, a formulation is considered physically stable if no more than about 15% aggregates are formed after at least one year of storage at the intended storage temperature of the product (e.g., refrigerated storage or subzero storage); or storage of the product at 25° C./60% relative humidity for one month, two months, and preferably at least three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

"Stable formulation" refers to a formulation where at least about 65% of the therapeutic agents (e.g., peptides or salts thereof) remain chemically and physically stable after at least one month of storage at room temperature, or up to at least one year of storage at refrigerated or subzero temperatures. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta, or electron beam).

As used herein, "parenteral injection" refers to the administration of therapeutic agents (e.g., peptides or small molecules) via a route other than the alimentary canal—any administration that is not by way of the digestive tract—for example, intravenous infusion, intranasal administration, buccal administration, transdermal administration, or injection under or through one or more layers of skin or mucus membranes of an animal, such as a human. Standard parenteral injections are given into the subcutaneous, intramuscular, or intradermal tissues of an animal, e.g., a human. These deep locations are targeted because the tissue expands more easily relative to shallow dermal sites to accommodate injection volumes required to deliver most therapeutic agents, e.g., 0.1 to 3.0 cc (mL).

The term "intracutaneous" encompasses administration into the epidermal, dermal or subcutaneous skin layer.

As used herein, the term "aprotic polar solvent" refers to a polar solvent which does not contain acidic hydrogen and thus does not act as a hydrogen bond donor. Polar aprotic solvents include, but are not limited to dimethylsulfoxide (DMSO), dimethylformamide (DMF), ethyl acetate, n-methyl pyrrolidone (NMP), dimethylacetamide (DMA), and propylene carbonate.

As used herein, the term "aprotic polar solvent system" refers to a solution wherein the solvent is a single aprotic polar solvent (for example, neat DMSO), or a mixture of two or more aprotic polar solvents (for example, a mixture of DMSO and NMP), or a mixture of at least one aprotic polar solvent with another pharmaceutically acceptable solvent system. In additional aspects, the term "aprotic polar solvent system" refers to a solution wherein the solvent is one or more aprotic polar solvents admixed with an amount of moisture, e.g., water, at a v/v ratio of at least about 99.9% aprotic solvent to about 0.1% water, up to a v/v ratio of at least about 50% aprotic solvent to about 50% water.

As used herein, "residual moisture" may refer to the residual moisture (typically, residual water) in the drug powder following preparation by the manufacturer/supplier. Typical powders often have residual moisture contents ranging from up to 10% (w/w). When these powders are dissolved in an aprotic polar solvent system, the residual moisture in the powder is incorporated into the formulation. Additionally, the aprotic polar solvents may also contain a certain level of residual moisture. For example, a freshly opened bottle of USP-grade DMSO may contain up to 0.1% (w/w) moisture. The residual moisture is different from "added moisture," where water is intentionally added to the formulation, for example to serve as a co-solvent, or to depress the freezing point of the aprotic polar solvent system. Moisture may also be introduced into the formulation during addition of an ionization stabilizing excipient (for example, through addition of a mineral acid from an aqueous stock solution (e.g. 1 N HCl or $H_2SO_4$)), or through the addition of water (e.g. water for injection). The total moisture content (% v/v, unless otherwise stated) in a formulation immediately following preparation is due to the contributions from both the residual moisture and the added moisture.

As used herein, "device flow path" refers to a part of a device that can come into contact with a formulation/solution/solvent, during administering the formulation/solution/solvent to a subject using the device. In some aspects the device can be an infusion set in series with a pump capable of parenterally administering a formulation/solution/solvent to a subject through various needles and/or tubing. In other aspects the device can be a patch pump that is directly adhered to the patient and which does not require the use of an external infusion set connected in series with the pump.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

"Pharmaceutically acceptable carrier" means a pharmaceutically acceptable solvent, suspending agent, or vehicle for delivering a drug compound of the present invention to a mammal such as a human.

As used herein an "ionization stabilizing excipient" is an excipient that establishes and/or maintains a particular ionization state for a therapeutic agent. In certain aspects the ionization stabilizing excipient can be, or includes, a molecule that donates at least one cation, particularly at least one divalent cation, under appropriate conditions or that is a cation (particularly a divalent cation)-donating compound or source.

As used herein a "mineral acid" is an acid that is derived from one or more inorganic compounds. Accordingly, mineral acids may also be referred to as "inorganic acids." Mineral acids may be monoprotic or polyprotic (e.g. diprotic, triprotic, etc.).

Non-limiting examples of mineral acids include hydrochloric acid (HCl), nitric acid ($HNO_3$), sulfuric acid ($H_2SO_4$), and phosphoric acid ($H_3PO_4$).

As used herein a "mineral base" (which may be equally and alternatively referred to as an "inorganic base") is a base that is derived from one or more inorganic compounds. Many, but not all, inorganic bases are generally classified as "strong bases," and non-limiting examples of inorganic bases include sodium hydroxide (NaOH), potassium hydroxide (KOH), magnesium hydroxide ($Mg(OH)_2$) and calcium hydroxide ($Ca(OH)_2$).

As used herein an "organic acid" is an organic compound with acidic properties (i.e. can function as a proton source). Carboxylic acids, such as acetic acid or citric acid, are one example of organic acids. Other known examples of organic acids include, but are not limited to, alcohols, thiols, enols, phenols, and sulfonic acids. Organic acids may be monoprotic or polyprotic (e.g. diprotic, triprotic, etc.).

As used herein an "organic base" is an organic compound with basic properties (i.e., it can function as a proton acceptor/sink). Many, but not all, organic bases contain nitrogen atoms (e.g., amines), and non-limiting examples of organic bases include amino acids (e.g., histidine, arginine, lysine), pyridine, imidazole and tromethamine. Organic bases may accept one or more protons per molecule.

"Charge profile," "charge state," "ionization," "ionization state," and "ionization profile" may be used interchangeably and refer to the ionization state due to protonation and/or deprotonation of the peptide's ionogenic groups.

As used herein, a "co-formulation" is a formulation that contains two or more therapeutic agents dissolved in an aprotic polar solvent system. The therapeutic agents may belong to the same class (for example, a co-formulation comprising two or more therapeutic peptides, such as insulin and pramlintide, or glucagon and GLP-1), or the therapeutic agents may belong to different classes (for example a co-formulation comprising one or more therapeutic small molecules and one or more therapeutic peptide molecules, such as GLP-1 and lisofylline).

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1A: formulation A-1; FIG. 1B: formulation A-2 (see Table 1 in Example 1 hereinbelow for formulation components).

FIGS. 2A and 2B are ordered, from left to right, as follows: Non-SR (control); Formulation A-1; Formulation A-2; Formulation B-1; Formulation B-2; Formulation C-1; Formulation C-2. See Table 1 in Example 1 hereinbelow for formulation components.

FIGS. 3A and 3B are ordered, from left to right, as follows: Non-SR (control); Formulation A-1; Formulation A-2; Formulation B-1; Formulation B-2; Formulation C-1; Formulation C-2. See Table 1 in Example 1 hereinbelow for formulation components.

FIGS. 4A and 4B are ordered, from left to right, as follows: Non-SR (control); Formulation A-1; Formulation A-2; Formulation B-1; Formulation B-2; Formulation C-1; Formulation C-2. See Table 1 in Example 1 hereinbelow for formulation components.

FIGS. 5A and 5B are ordered, from left to right, as follows: Non-SR (control); Formulation A-1; Formulation A-2; Formulation B-1; Formulation B-2; Formulation C-1; Formulation C-2. See Table 1 in Example 1 hereinbelow for formulation components.

(FIGS. 7A, 7B) or 25° C. (FIGS. 7C, 7D). See Table 1 in Example 1 hereinbelow for formulation components.

FIG. 8A: formulation groups 1-5; FIG. 8B: formulation groups 1 and 6-8. See Table 3 in Example 2 hereinbelow for formulation components.

(FIG. 9A), 5° C. (FIG. 9B), 25° C. (FIG. 9C) or 40° C. (FIG. 9D). IR: immediate-release GVOKE® glucagon (100 mg/mL glucagon, 126 mM $H_2SO_4$); A: 100 mg/mL glucagon, 126 mM $H_2SO_4$, 40% ester-terminated PLGA; B: 100 mg/mL glucagon, 126 mM $H_2SO_4$, 5% (w/v) trehalose, 40% ester-terminated PLGA; C: 100 mg/mL glucagon, 126 mM $H_2SO_4$, 40% acid-terminated PLGA.

FIG. 11A: formulation comprising 250 mg/mL glucagon, 40% Resomer® RG502 PLGA in acidified DMSO; FIG. 11B: formulations comprising 100 mg/mL glucagon, 40% Resomer® RG502 PLGA in acidified DMSO (bottom line) or 100 mg/mL glucagon, 40% Resomer® RG502H PLGA in acidified DMSO (top line)

DETAILED DESCRIPTION OF THE INVENTION

Figures 1A, 1B:
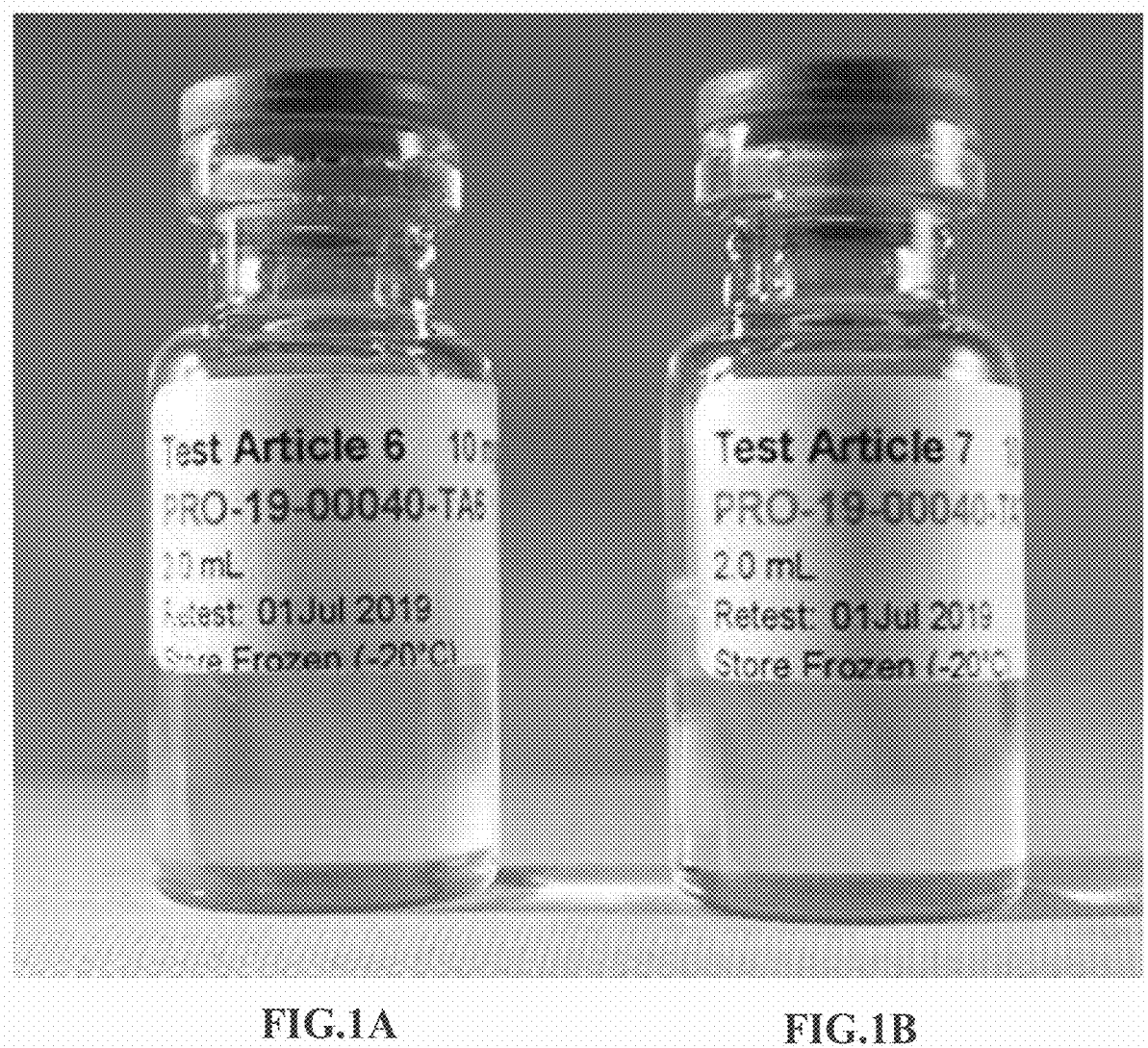
FIGS. 1A-1B are photographs demonstrating a visual assessment of the physical appearance of exemplary formulations of the invention immediately after formulation (i.e., at T=0).
Figure 2A:
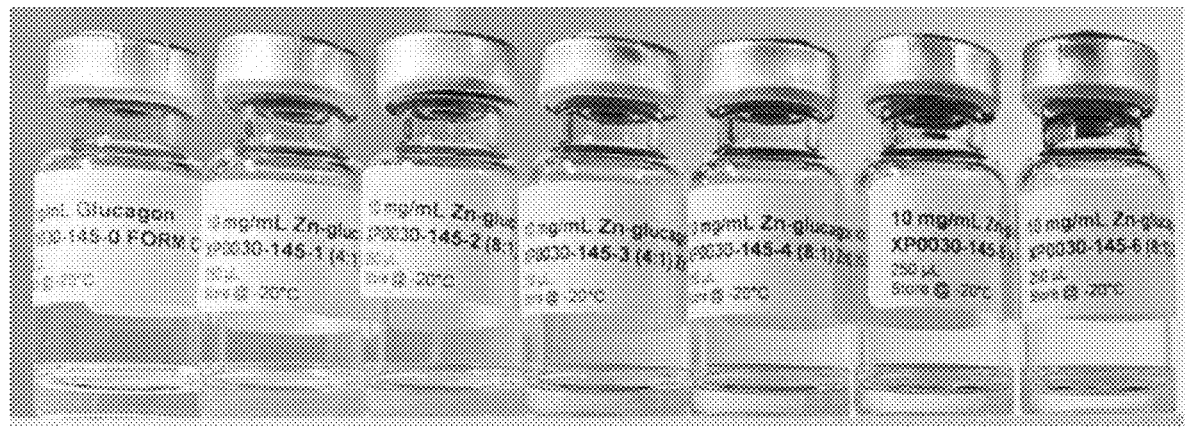
FIGS. 2A-2B are a series of photographs demonstrating the stability of SR glucagon formulations of the invention. Samples were photographed following storage for 6 months at −20° C. and examined visually for evidence of glucagon degradation (e.g., discoloration, precipitation, gelation, aggregation). Images were photographed against a white background (FIG. 2A) to show any visible discoloration or against a black background (FIG. 2B) to show any visible aggregation/fibrillation, vs. a control (non-SR) glucagon formulation. Samples in both
Figure 2B:
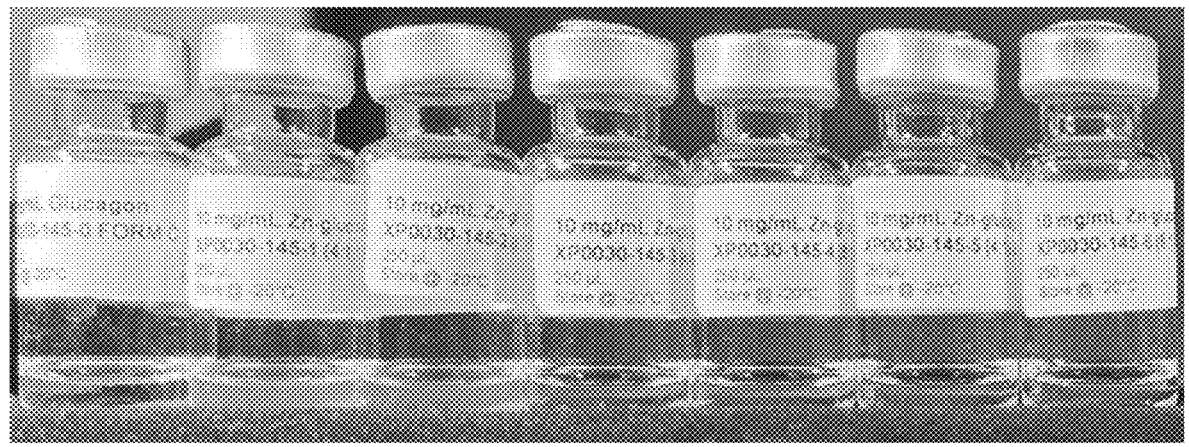
Figure 3A:
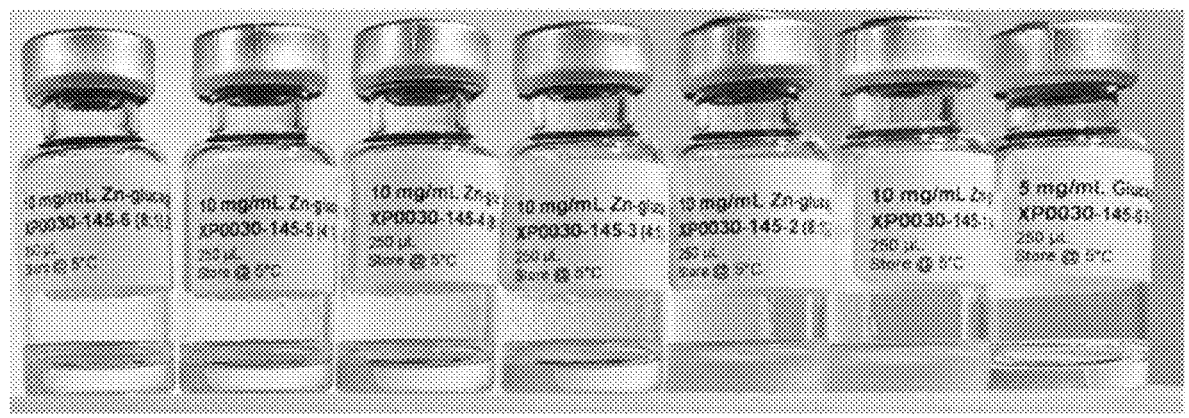
FIGS. 3A-3B are a series of photographs demonstrating the stability of SR glucagon formulations of the invention. Samples were photographed following storage for 6 months at 5° C. and examined visually for evidence of glucagon degradation (e.g., discoloration, precipitation, gelation, aggregation). Images were photographed against a white background (FIG. 3A) to show any visible discoloration or against a black background (FIG. 3B) to show any visible aggregation/fibrillation, vs. a control (non-SR) glucagon formulation. Samples in both
Figure 3B:
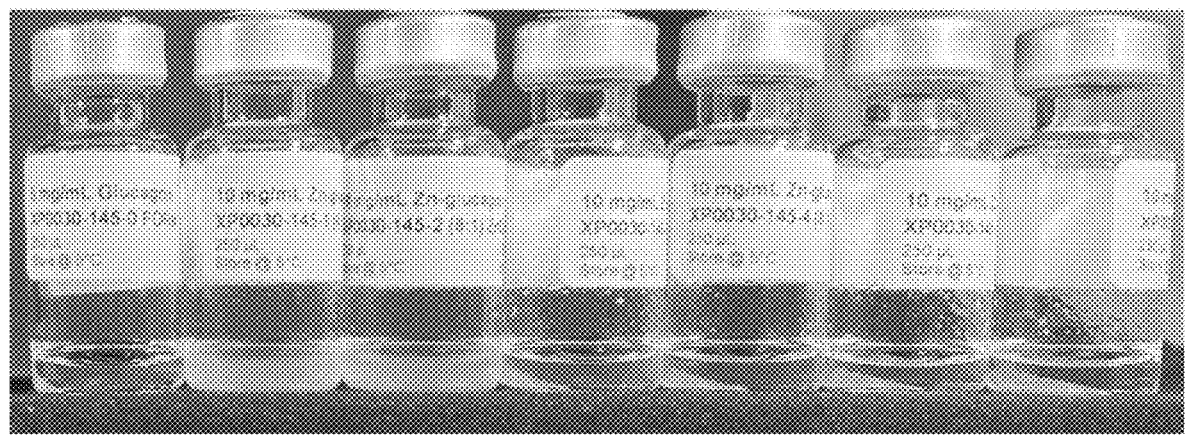
Figure 4A:
FIGS. 4A-4B are a series of photographs demonstrating the stability of SR glucagon formulations of the invention. Samples were photographed following storage for 6 months at 25° C. and examined visually for evidence of glucagon degradation (e.g., discoloration, precipitation, gelation, aggregation). Images were photographed against a white background (FIG. 4A) to show any visible discoloration or against a black background (FIG. 4B) to show any visible aggregation/fibrillation, vs. a control (non-SR) glucagon formulation. Samples in both
Figure 4B:
Figure 5A:
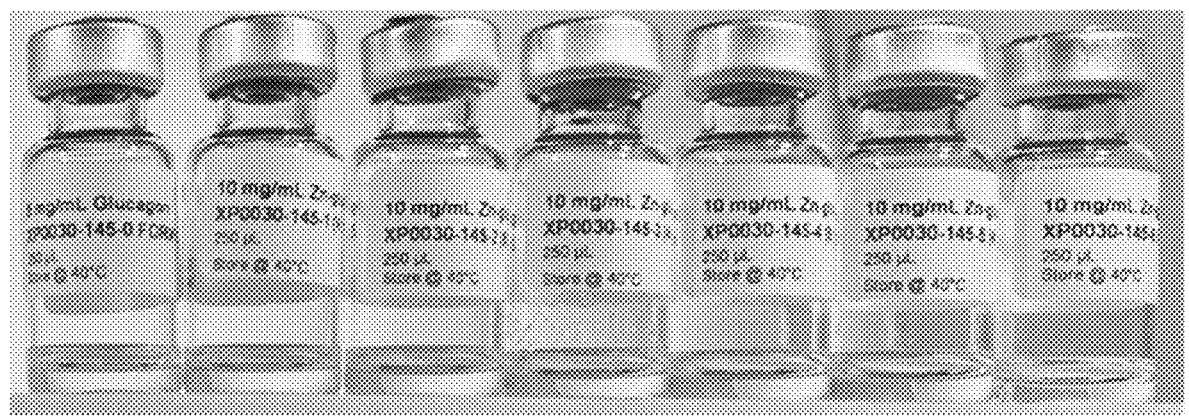
FIGS. 5A-5B are a series of photographs demonstrating the stability of SR glucagon formulations of the invention. Samples were photographed following storage for 6 months at 40° C./75% relative humidity and examined visually for evidence of glucagon degradation (e.g., discoloration, precipitation, gelation, aggregation). Images were photographed against a white background (FIG. 5A) to show any visible discoloration or against a black background (FIG. 5B) to show any visible aggregation/fibrillation, vs. a control (non-SR) glucagon formulation. Samples in both
Figure 5B:
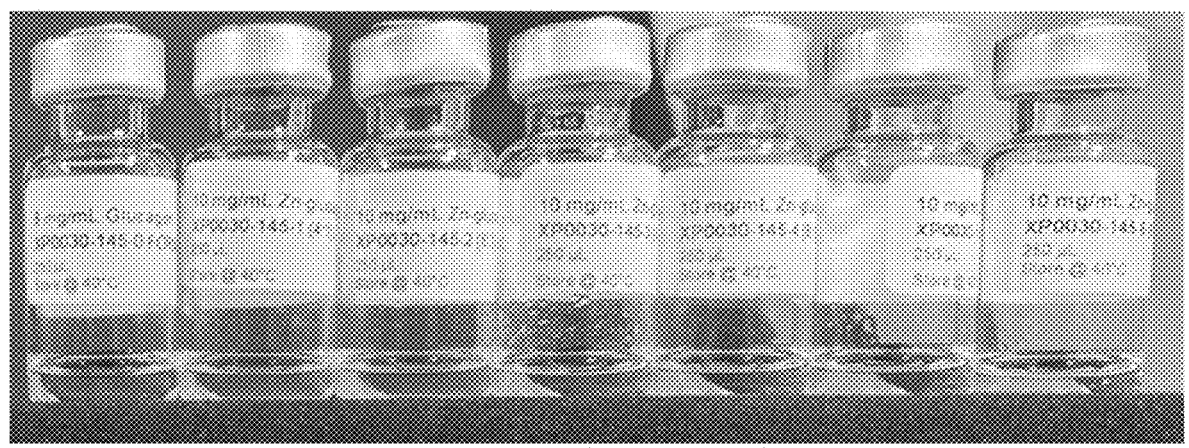

When prepared as aqueous solutions, standard small molecule, peptide, and protein molecules may be susceptible to multiple physical and chemical degradative pathways. For many of these therapeutic molecules, degradation pathways that are catalyzed, mediated and/or promoted by water (e.g., hydrolysis, racemization, deamidation) cannot be avoided and consequently the molecule cannot be adequately stabilized. Accordingly, many therapeutic agents cannot be prepared as stable solutions for parenteral injection and are instead prepared as powders that are reconstituted immediately prior to use.

To address the physical and/or chemical instability that many therapeutic molecules exhibit in water, formulations may be prepared wherein the therapeutic agent is dissolved in a biocompatible non-aqueous liquid, such as an aprotic polar solvent (e.g. DMSO). Previous non-aqueous formulations are at least partially based on the premise that limiting the moisture content of the formulation promotes physical and chemical stability by inhibiting water-mediated degradation pathways. Many of these known formulations limit the moisture content to at most 10% (w/w).

The use of aprotic polar solvents to prepare non-aqueous therapeutic formulations to inhibit many common degradation pathways, particularly those involving water, can significantly improve the stability of the solubilized or dissolved therapeutic molecule(s). However, problems still remain with the compositions and methods disclosed in the art. In particular, direct dissolution of a therapeutic molecule in an aprotic polar solvent is not a suitable approach for preparing stable compositions of most therapeutic molecules. Various therapeutics when solubilized directly in DMSO, for example glucagon at a concentration of 5 mg/mL, will form insoluble aggregates within one day of storage at room temperature. For a composition comprising only glucagon and DMSO, 5 mg/mL corresponds to approximately 0.45% (w/w) of the peptide compound, indicating that at even relatively low concentrations, direct dissolution in an aprotic polar solvent system is by itself incapable of preventing physical aggregation and/or gelation of a therapeutic molecule. Moreover, therapeutic molecules that may not form insoluble aggregates in an aprotic polar solvent system may nonetheless be prone to chemical degradation when solubilized directly in an aprotic polar solvent system.

Without wishing to be bound by theory, it is thought that in order to exhibit enhanced or optimal stability and solubility when formulated in an aprotic polar solvent system, a therapeutic molecule may require a specific ionization profile. The ionization profile is the charge state acquired via protonation and/or deprotonation of the therapeutic molecule's ionogenic groups. For example, protonation of the ionogenic amino acid residues (e.g., arginine, lysine, aspartic acid, glutamic acid) comprising a therapeutic peptide may confer an overall positive charge on the molecules in solution. Alternatively, deprotonation of ionogenic amino acid residues may confer an overall negative charge on the molecules in solution. For the non-limiting examples used herein, protonated (i.e. positively charged) molecules will be described, although the deprotonation of ionogenic amino acid residues in therapeutic peptide molecules is also considered to be within the scope of the present invention. The relatively long-range electrostatic repulsions between positively charged peptide molecules may inhibit the short-range hydrophobic interactions that can result in physical aggregation and/or gelation. Thus, in the absence of sufficient protonation (i.e., an optimal or beneficial ionization profile), therapeutic molecules dissolved in an aprotic polar solvent system may be physically unstable and lead to the formation of soluble and/or insoluble aggregates. Accordingly, it may be necessary to include at least one excipient in a sufficient concentration to function as an ionization stabilizing agent that is capable of imparting the ionization profile for improved physical and/or chemical stability to the active agent in the aprotic polar solvent system. The appropriate concentration of the ionization stabilizing excipient(s) to be added to the a solution depends on several factors including, but not limited to, the chemical structure of the ionization stabilizing excipient, the chemical structure of the active agent(s), the concentration of the active(s), the solvent system used, the presence of co-solvents, and the presence of additional excipients or formulation components and their respective concentrations.

Certain compositions and methods are designed to establish an optimal ionization profile for therapeutic molecules before they are solubilized in an aprotic polar solvent system. For example, a peptide powder from a supplier/manufacturer is initially dissolved in a buffered aqueous solution where the pH of the buffered aqueous peptide solution is set to that of optimal stability and solubility for the specific peptide. The peptide is then dried (for example via freeze drying or spray drying) to a powder from the aqueous solution such that the ionization profile of the peptide molecule in the powder may be about equal to the ionization profile of the peptide molecule in the aqueous solution from which it was dried. When the peptide powder is then solubilized in an aprotic polar solvent system, the ionization profile of the peptide molecule may be about equal to the ionization profile of the peptide molecule in the powder. Accordingly, the ionization profile of the peptide molecule in the aprotic polar solvent system is about equal to the ionization profile of the peptide molecule in the buffered aqueous solution.

The requirement for drying a therapeutic molecule from a buffered aqueous solution in order to optimize the ionization profile of the molecule and impart pH memory before it is solubilized in an aprotic polar solvent often imposes significant added costs, both in terms of time and expense, to the formulation development pathway. In particular, the drying process is well known to impose several stresses on the therapeutic molecule, and additional excipients (e.g., lyoprotectants such as trehalose and sucrose, and/or surfactants such as polysorbate 80) must be included in the aqueous solution in sufficient amounts to protect the therapeutic molecule, thereby increasing the cost and complexity of the formulation. Further, the drying process (e.g., spray drying, freeze drying) must often be optimized for a given therapeutic molecule, both at the lab-scale during initial research and development where the process is initially developed, and then during the manufacturing-scale as the process is scaled-up and transferred to instruments and facilities capable of producing commercial-scale batches. Consequently, the combination of initially developing and optimizing a drying process for a given therapeutic molecule, coupled with the time and costs associated with both transferring the method and incorporating an additional step in the manufacturing process can be very expensive. Without wishing to be bound by theory, it is believed that by providing a sufficient quantity of at least one ionization stabilizing excipient to achieve an appropriate or optimal ionization profile of the therapeutic molecule, electrostatic repulsion between therapeutic molecules possessing the same charge polarity (i.e. negatively or positively charged) may be sufficient in magnitude to prevent physical degradation (e.g., via short-range hydrophobic interaction between molecules that lead to aggregation). This is especially important for molecules that exhibit a tendency to aggregate in solution, particularly as the concentration of the molecule in solution is increased. Further, by controlling and optimizing the extent of the ionization (i.e., protonation or deprotonation) of the therapeutic agent, chemical degradation can be minimized, as, for example, an excess of protonation may promote chemical instability via degradative reactions such as oxidation (for example, oxidation of methionine residues) and fragmentation (for example, cleavage of the peptide backbone). Accordingly, for some therapeutic molecules there may be an optimal or beneficial ionization profile achieved via protonation or deprotonation such that physical and/or chemical degradation reactions are minimized. For a therapeutic peptide, the extent of ionization (i.e., protonation or deprotonation) required for stability, and thus the amount of the ionization stabilizing excipient required in the solution, will depend on, among other things, the primary structure (i.e., amino acid sequence) and the peptide concentration in the solution.

Each molecule that functions as an ionization stabilizing excipient will exhibit a certain tendency to donate protons to, or accept protons from, the therapeutic molecule(s) and/or additional drug substance/powder components (e.g. salts, counterions, buffer molecules, etc.) in a given solvent system; the tendency to donate protons may be referred to as the relative acidic strength of the molecule, while the tendency to accept protons may be referred to as the relative basic strength of the molecule. As a non-limiting example, for a fixed concentration of a proton-donating molecule, (and for simplicity it is assumed only monoprotic molecules in this example) molecules that have a greater acidic strength will protonate the therapeutic molecule to a greater extent than a weaker acid. Accordingly, the concentration of a given proton-donating molecule (ionization stabilizing excipient) required to achieve an appropriate or optimal ionization profile for the therapeutic molecules will be inversely proportional to its acidic strength. These and other non-limiting aspects of the present invention are discussed herein.

Storage stable SR formulations of the invention also comprise at least one sustained release modifier, which is a compound that conveys sustained release (SR) characteristics upon the therapeutic compound that is incorporated into the formulation. By "sustained release" is meant that the therapeutic agent contained in the formulation exhibits delayed or prolonged release kinetics in an aqueous environment, such as in the body of an animal (including a human) to whom the SR formulation has been administered, relative to an immediate release non-SR formulation of the same therapeutic compound that does not contain at least one sustained release modifier. Examples of sustained release modifiers suitable for use in accordance with such aspects of the invention include those that are cation-donating compounds (or cation-containing sources), particularly those that are divalent cation-donating (or divalent cation-containing sources). Suitable such compounds include salts of certain metals, including divalent salts of zinc, for example zinc sulfate, zinc chloride and zinc acetate; divalent salts of magnesium; divalent salts of manganese; divalent salts of calcium; divalent salts of iron; divalent salts of copper; and divalent salts of aluminum. Other suitable divalent salt compounds useful as sustained release modifiers according to this aspect of the invention are known in the art and will be familiar to those of ordinary skill. Such divalent cation compounds, when used as sustained release modifiers in producing the storage stable SR formulations of the present invention, are included in the formulations in a ratio of the salt to the therapeutic compound that is at least 1:1, and suitable 1:1, 2:1, 4:1, 5:1, 8:1, 10:1, 12:1, 15:1, 16:1, 20:1 or even higher. By way of non-limiting example, suitable storage stable SR glucagon formulations of the invention comprise a zinc salt (e.g., zinc sulfate, zinc chloride or zinc acetate) in a ratio of zinc:glucagon of 1:1, 2:1, 4:1, 8:1 or 16:1. Other suitable sustained release modifiers include one or more polymers, including but not limited to a poly(D,L-lactic-co-glycolic acid) ("PLGA") such as those available from Evonik (Parsippany, NJ) including Resomer® RG502 (an ester-terminated PLGA) and Resomer RG502H (an acid-terminated PLGA), a poly(ethylene glycol) ("PEG"), and the like. Suitable SR and even long-acting ("LA") formulations of peptides can be prepared using one or more PLGAs at varying concentrations in the formulations described herein, particularly at about 25% to about 50%, about 25% to about 45%, about 25% to about 40%, about 25% to about 35%, and about 25% to about 30%.

In certain aspects, the aprotic polar solvent can be deoxygenated prior to preparation of the formulation. Many different techniques can be used in the context of the present invention to deoxygenate or remove oxygen from aprotic polar solvents (degasification or deoxygenation). For instance, it is contemplated that deoxygenation can, but is not limited to, remove oxygen that is dissolved in a liquid aprotic polar solvent either by the liquid alone, by the liquid and other solute molecules (e.g. micelles, cyclodextrins, etc.), or by other solute molecules alone. Non-limiting examples of deoxygenation techniques include placing the aprotic polar solvent under reduced pressure and/or heating the liquid to decrease the solubility of dissolved gas, fractional distillation, membrane degasification, substitution by inert gas, using a reducing agent, freeze-pump-thaw cycling, or long time storage in a container with air-locks. In one embodiment, the aprotic polar solvent is deoxygenated by vacuum degasification. In another embodiment the aprotic polar solvent is deoxygenated by using a deaerator. In one instance, the deaerator is a tray-type or cascade type deaerator. In another instance, the deaerator is a spray-type deaerator. In yet another embodiment, the aprotic polar solvent is deoxygenated using a gas-liquid separation membrane. In one instance, the aprotic polar solvent is degassed using a gas-liquid separation membrane and reduced pressure. In one embodiment a non-oxygen gas (e.g., $N_2$) is bubbled through the liquid to replace or reduce oxygen in the aprotic polar solvent. In one instance, the gas bubbled through the aprotic polar solvent is argon, helium, nitrogen, an inert gas, and/or hydrogen gas, preferably nitrogen gas. In another instance the gas is bubbled through the aprotic polar solvent using a gas-stripping column. In yet another embodiment, the aprotic polar solvent is deoxygenated by one or more reducing agent(s). Non-limiting examples of reducing agents include ammonium sulfite, hydrogen gas, active deoxygenating metals, copper, tin, cadmium, Wood's metal alloy (50% bismuth, 25% lead, 12.5% tin, and 12.5% cadmium), etc. In yet another embodiment the aprotic polar solvent is degassed by freeze-pump-thaw cycling (e.g., at least 1, 2, 3, or more cycles can be used). In one instance the freeze-pump-thaw cycle comprises freezing the aprotic polar solvent under liquid nitrogen, applying a vacuum, and then thawing the solvent in warm water. In one embodiment the aprotic polar solvent is deoxygenated by long time storage in a steel, glass, or wood container. In another embodiment, the aprotic polar solvent is sonicated, ultrasonicated, or stirred during deoxygenation.

Once treated or deoxygenated, the aprotic polar solvents may have less than 0.1 mM of dissolved oxygen, preferably less than 0.05 mM of dissolved oxygen. Methods known to those of skill in the art can be used to determine the amount of dissolved oxygen in any given aprotic polar solvent (e.g., a dissolved oxygen meter or probe device can be used such as the Dissolved Oxygen Probe commercially available by Vernier (Beaverton, Oregon, USA)).

In certain aspects the formulations disclosed in the present application can be prepared and/or sealed under an inert gas atmosphere. Common methods include backfilling the primary container-closure system (e.g. vials) to provide an inert gas (e.g. nitrogen, argon) headspace. A secondary container-closure system (e.g. sealed foil pouches) may also be sealed under an inert gas environment.

I. Formulations

Formulations of the present invention include a therapeutic agent present in an aprotic polar solvent system containing at least one ionization stabilizing excipient that is compatible with the container and/or fluid flow path, and at least one sustained release modifier. The therapeutic agent can be dissolved (e.g., fully or partially solubilized) or suspended (fully or partially) in the aprotic polar solvent system.

In some embodiments, the therapeutic agent is present in an aprotic polar solvent that is "neat," i.e., that does not contain a co-solvent or, if it contains a co-solvent does not contain a co-solvent other than water. In other embodiments the therapeutic agent is present in a solvent system that is a mixture of two or more aprotic polar solvents and a moisture or water content greater than 10% v/v (i.e., an aprotic polar solvent system). An example would be a 75/25 (% v/v) mixture of DMSO and NMP with a total moisture content of greater than 10% (v/v). In some embodiments, however, a co-solvent can be used, where in one or more aprotic polar solvents are mixed with a co-solvent. Non-limiting examples of co-solvents include (explicitly excluding water) ethanol, propylene glycol (PG), glycerol, and mixtures thereof. The co-solvent may be present in the formulation in an amount ranging from about 0.1% (w/v) to about 50% (w/v), e.g., about 0.1%, about 0.5%, about 1%, about 5%, about 10%, about 15%, about 20%, about 25%, about 30%, about 35%, or about 40% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Still further, the formulations of the present invention can include one or more other excipients in addition to the at least one ionization stabilizing excipient and the at least one sustained release modifier. In some embodiments, the other excipient is selected from sugars, salts, starches, sugar alcohols, antioxidants, chelators, and preservatives. Examples of suitable sugars excipients include, but are not limited to trehalose, glucose, sucrose, etc. Examples of suitable starches for stabilizing excipients include, but are not limited to, hydroxyethyl starch (HES). Examples of suitable sugar alcohols (also referred to as polyols) for stabilizing excipients include, but are not limited to, mannitol and sorbitol. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, EDTA disodium salt (edetate disodium), tartaric acid and salts thereof, glycerin, and citric acid and salts thereof. Examples of suitable inorganic salts include, but are not limited to, sodium chloride, potassium chloride, calcium chloride, magnesium chloride, calcium sulfate, magnesium sulfate, zinc sulfate and zinc acetate. Examples of suitable preservatives include, but are not limited to, benzyl alcohols, methyl parabens, metacresol, propyl parabens, and mixtures thereof. Additional formulation components include local anesthetics, such as lidocaine or procaine. In some embodiments, the additional stabilizing excipient is present in the formulation in an amount ranging from about 0.01% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the additional stabilizing excipient is present in the formulation in an amount that is about, at most, or at least 0.01, 0.1, 0.5, 1, 2, 3, 4, 5, 6, 7, 8, 9, 10, 15, 20, 25, 30, 35, 40, 45, 50, 55, or 60% (w/v).

II. Therapeutic Agents

Therapeutic agents in the context of the present invention encompass peptide or protein compounds, small molecule drugs, and pharmaceutically acceptable analogs and/or salts thereof. One of skill is aware of which therapeutic agent is suitable for treating certain diseases or conditions and would be capable of administering effective amounts of a therapeutic agent in a formulation as described herein for the treatment of a disease or condition.

Non-limiting examples of peptides and proteins (and salts thereof) that can be used in the context of the present invention include, but are not limited to, glucagon, pramlintide, insulin, leuprolide, an luteinizing-hormone-releasing hormone (LHRH) agonist, adrenocorticotropic hormone (ACTH), leuprolide, hirudin, parathyroid hormone (PTH), amylin, angiotensin(1-7), botulinum toxin, hematide, an amyloid peptide, gastric inhibitory peptide, an antibody (which may be monoclonal or polyclonal) or a fragment thereof, an immunogenic peptide (e.g., a peptide or peptide complex derived from a virus, a bacterium, or any prokaryotic or eukaryotic organism or cell thereof), an insulin-like growth factor, growth hormone releasing factor, anti-microbial factor, glatiramer, glucagon-like peptide-1 (GLP-1), a GLP-1 agonist, exenatide, analogs thereof, an amylin analog (pramlintide), and mixtures thereof. In some preferred aspects the therapeutic agent is glucagon, insulin and/or pramlintide. Additional suitable examples of such peptides, proteins, peptide complexes and derivatives thereof that may be advantageously used in the compositions and methods of the present invention will be familiar to the ordinarily skilled artisan based on information that is provided herein and that is readily available in the art.

Non-limiting examples of small molecule drugs (and salts thereof) that can be used in the context of the present invention include, but are not limited to, epinephrine, benzodiazepines, levothyroxine, catecholemines, "triptans," sumatriptan, novantrone, chemotherapy small molecules (e.g., mitoxantrone), corticosteroid small molecules (e.g., methylprednisolone, beclomethasone dipropionate), immunosuppressive small molecules (e.g., azathioprine, cladribine, cyclophosphamide monohydrate, methotrexate), anti-inflammatory small molecules (e.g., salicylic acid, acetylsalicylic acid, lisofylline, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, metrifonate, rivastigmine, selegilene, imipramine, fluoxetine, olanzapine, sertindole, risperidone, valproate semisodium, gabapentin, carbamazepine, topiramate, phenytoin), small molecules used to treat cancer (e.g., vincristine, vinblastine, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives, small molecules used to treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule β-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine). In preferred embodiments, the small molecule is epinephrine.

The therapeutic agent of the invention can be administered intracutaneously in the prevention, diagnosis, alleviation, treatment, or cure of disease. Examples of proteins and proteinaceous compounds which may be formulated and employed in the delivery system according to the present invention include those proteins which have biological activity or which may be used to treat a disease or other pathological conditions.

Each of the aforementioned peptides, proteins, and small molecule drugs are well-known and commercially available from a variety of manufacturers and sources. Further, the amount of the peptides, proteins, or small molecule drugs in the dosage formulations can be varied depending on currently acceptable amounts, subject/patient needs (e.g., age, health, weight, nature and extend of symptom), and the like; such amounts are readily determined by one of ordinary skill in the pharmaceutical and pharmacological arts based on information that is readily available.

The therapeutic agents provided by the manufacturer or commercial source are typically provided in a powdered form for dissolution into the formulations as described herein. A number of known techniques can be used to form a powdered agent for dissolution.

Any suitable dosage of peptide or peptides can be formulated in the stable formulations of the present invention. Generally, the peptide (or, in embodiments comprising two or more peptides, each of the peptides) is present in the formulation in an amount ranging from about 0.1 mg/mL up to the solubility limit of the peptide or peptides. In certain such embodiments, the dosage is from about 0.1 mg/mL to about 500 mg/mL, or up to about 200 mg/mL, about 250 mg/mL, about 300 mg/mL, about 350 mg/mL, about 400 mg/mL, about 450 mg/mL or about 500 mg/mL. In some embodiments, the peptide is present in the formulation in an amount ranging from about 2 mg/mL to about 60 mg/mL. In other embodiments, the peptide is present in the formulation in an amount ranging from about 3 mg/mL to about 50 mg/mL. In still other embodiments, the peptide is present in the formulation in an amount ranging from about 5 mg/mL to about 15 mg/mL. In yet other embodiments, the peptide is present in the formulation in an amount ranging from about 0.1 mg/mL to about 10 mg/mL (e.g., about 0.5 mg/mL, about 1 mg/mL, about 2 mg/mL, about 2.5 mg/mL, about 3 mg/mL, about 4 mg/mL, about 5 mg/mL, about 7.5 mg/mL or about 10 mg/mL). In yet other embodiments, the peptide is present in the formulation in an amount ranging from about 1 mg/mL to about 50 mg/mL. Again, it will be readily apparent to those of skill that the peptide dosage can be varied depending on the peptide used and the disease, disorder or condition to be treated, based on information provided herein and that is readily available in the relevant arts.

In some embodiments, the formulations of the present invention further comprise an antioxidant. In other embodiments, the formulations further comprise a chelator. In still other embodiments, the formulations of the present invention further comprise a preservative, sugar (e.g., a monosaccharide, a disaccharide or a polysaccharide, e.g., threhalose dihydrate), a sugar alcohol (e.g., mannitol, xylitol or erythritol), a polyol, a surfactant and/or a salt.

III. Therapeutic Methods

In another aspect, the present invention provides methods of treating or preventing diseases, conditions, or disorders by administering to a subject a therapeutic agent for treating or preventing a disease, condition, or disorder in a stable formulation as described herein in an amount effective to treat, alleviate, ameliorate or prevent the disease, condition, or disorder.

In some embodiments, a therapeutic method of the present invention comprises treating hypoglycemia by administering to a subject having hypoglycemia a therapeutic agent for hypoglycemia in a storage stable SR formulation as described herein in an amount effective to treat the hypoglycemia. In some embodiments, the subject is administered a storage stable SR formulation comprising glucagon, in a manner that results in the release of glucagon from the site of administration into the bloodstream or tissues of the animal over a prolonged period of time (i.e., "sustained release") when compared to a non-SR (or "immediate release") formulation comprising glucagon. In certain aspects hypoglycemia can be caused by diabetes (including Type 1 or Type 2 diabetes, exercise-induced or-associated diabetes, post-bariatric diabetes, gestational diabetes, nocturnal diabetes, and the like) or non-diabetes related diseases, conditions, and disorders.

As described by the Workgroup of the American Diabetes Association and the Endocrine Society, (Seaquist, et al, (2013), *Diabetes Care*, Vol 36, pages 1384-1395) with respect to hypoglycemia a single threshold value for plasma glucose concentration that defines hypoglycemia in diabetes is not typically assigned because glycemic thresholds for symptoms of hypoglycemia (among other responses) shift to lower plasma glucose concentrations after recent antecedent hypoglycemia and to higher plasma glucose concentrations in patients with poorly controlled diabetes and infrequent hypoglycemia.

Nonetheless, an alert value can be defined that draws the attention of both patients and caregivers to the potential harm associated with hypoglycemia. Patients at risk for hypoglycemia (i.e., those treated with a sulfonylurea, glinide, or insulin) should be alert to the possibility of developing hypoglycemia at a self-monitored plasma glucose—or continuous glucose monitoring subcutaneous glucose—concentration of ≤70 mg/dL (≤3.9 mmol/L). Because it is higher than the glycemic threshold for symptoms in both nondiabetic individuals and those with well-controlled diabetes, it generally allows time to prevent a clinical hypoglycemic episode and provides some margin for the limited accuracy of monitoring device at low-glucose levels.

The condition of severe hypoglycemia is an event requiring assistance of another person to actively administer carbohydrates, glucagon, or take other corrective actions. Plasma glucose concentrations may not be available during an event, but neurological recovery following the return of plasma glucose to normal is considered sufficient evidence that the event was induced by a low plasma glucose concentration. Typically, these events begin occurring at plasma glucose concentrations of ≤50 mg/dL (2.8 mmol/L). Documented symptomatic hypoglycemia is an event during which typical symptoms of hypoglycemia are accompanied by a measured plasma glucose concentration≤70 mg/dL (≤3.9 mmol/L). Asymptomatic hypoglycemia is an event not accompanied by typical symptoms of hypoglycemia but with a measured plasma glucose concentration≤70 mg/dL (≤3.9 mmol/L). Probable symptomatic hypoglycemia is an event during which symptoms typical of hypoglycemia are not accompanied by a plasma glucose determination but that was presumably caused by a plasma glucose concentration≤70 mg/dL (≤3.9 mmol/L). Pseudo-hypoglycemia is an event during which the person with diabetes reports any of the typical symptoms of hypoglycemia with a measured plasma glucose concentration>70 mg/dL (>3.9 mmol/L) but approaching that level.

Further included in the indications which may be treated by the disclosed invention are hypoglycemia-associated autonomic failure (HAAF). As described by Philip E. Cryer, Perspectives in Diabetes, Mechanisms of Hypoglycemia-Associated Autonomic Failure and Its Component Syndromes in Diabetes, Diabetes, Vol. 54, pp. 3592-3601 (2005), "recent antecedent iatrogenic hypoglycemia causes both defective glucose counter-regulation (by reducing epinephrine responses to a given level of subsequent hypoglycemia in the setting of absent decrements in insulin and absent increments in glucagon) and hypoglycemia unawareness (by reducing sympathoadrenal and the resulting neurogenic symptom responses to a given level of subsequent hypoglycemia) and thus a vicious cycle of hypoglycemia." HAAF affects those with type 1 and advanced type 2 diabetes. Additionally, the invention of the present disclosure may also treat hypoglycemia in patients following islet cell transplantation.

The formulations of the present invention can also be used for the treatment of hyperinsulinemic hypoglycemia, which broadly refers to the condition and effects of low blood glucose levels that are caused by excessive insulin. The most common type of severe, but typically transient, hyperinsulinemic hypoglycemia arises from the administration of exogenous insulin in patients with Type 1 diabetes. This type of hypoglycemia can be defined as iatrogenic hypoglycemia and is a limiting factor in the glycemic management of type 1 and type 2 diabetes. Nocturnal hypoglycemia (night-time hypo) is a common type of iatrogenic hypoglycemia arising in patients taking exogenous insulin. However, hyperinsulinemic hypoglycemia can also arise due to endogenous insulin, for example in congenital hyperinsulinism, insulinomas (insulin-secreting tumors), exercise-induced hypoglycemia and reactive hypoglycemia. Reactive hypoglycemia is a non-diabetic hypoglycemia and is due to low blood sugar that occurs following a meal—typically within four hours after eating. Reactive hypoglycemia may also be referred to as postprandial hypoglycemia. Symptoms and signs of reactive hypoglycemia can include hunger, weakness, shakiness, sleepiness, sweating, confusion and anxiety. Stomach surgery (e.g. bariatric surgery) is one possible cause, as following surgery food may pass too quickly into the small intestine (e.g. post-bariatric hypoglycemia (PBH)). Additional causes include enzyme deficiencies that make it difficult for the body to breakdown food, or increased sensitivity to the hormone epinephrine.

In some embodiments, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia, including but not limited to diabetes-related hypoglycemia, exercise-induced hypoglycemia, and post-bariatric surgery hypoglycemia, or other types of hypoglycemia described herein and known to those of ordinary skill in the art. In some embodiments, the disease, condition, or disorder is diabetes.

In some embodiments, a therapeutic method of the present invention comprises treating diabetes by administering to a subject having diabetes a therapeutic agent in a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

In certain aspects epinephrine can be administered to a subject at risk of or suspected of anaphylaxis. Epinephrine is indicated as an emergency treatment of Type I allergic reactions which can arise from multiple sources, including, but not limited to, foods, drugs and/or other allergens, allergen immunotherapy, diagnostic testing substances, insect stings and bites, and idiopathic or exercise-induced anaphylaxis.

Administered dosages for the peptide or small molecule drugs as described herein for treating a disease, condition, or disorder (e.g., a diabetic condition, hypoglycemia, or anaphylaxis) are in accordance with dosages and scheduling regimens practiced by those of skill in the art. General guidance for appropriate dosages of all pharmacological agents used in the present methods is provided in Goodman and Gilman's The Pharmacological Basis of Therapeutics, 11th Edition, 2006, supra, and in the Physicians' Desk Reference (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a peptide drug. The dosage can be increased or decreased over time, as required by an individual patient or determined by medical personnel.

Determination of an effective amount or dose is well within the capability of those skilled in the art, especially in light of the detailed disclosure provided herein. Generally, the formulations to deliver these doses may contain one, two, three, four, or more small molecules, peptides, or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL. In certain aspects the concentration is about 1 mg/mL, about 2 mg/mL, about 2.5 mg/mL, about 3 mg/mL, about 4 mg/mL, about 5 mg/mL, about 7.5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. The concentrations for small molecules are known to medical personnel and can be established and implemented using the disclosure provided herein, e.g., 0.01 mg/ml to 500 mg/ml, or in doses of about 1, 2, 2.5, 3, 4, 5, 10, 25, 50, 75, 100, 200, 500, to about 1000 mg, including all values and ranges there between.

The formulations of the present invention may be used for parenteral administration, including, but not limited to, subcutaneous, intradermal, intramuscular, intranasal, buccal, transdermal or intravenous administration (e.g., by injection or by infusion). In some embodiments, the formulation is administered subcutaneously. The formulations can also be delivered transdermally, such as by topically applying the composition to skin (e.g., spreading the composition on skin or loading the composition onto a dermal patch and attaching the dermal patch to the skin).

The formulations of the present disclosure can be administered by infusion or by injection using any suitable device. For example, a formulation of the present invention may be placed into a syringe (e.g., a pre-filled syringe), a pen injection device, an auto-injector device, or a pump device. In some embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/auto injector devices include, but are not limited to, those pen/auto injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In some embodiments, the stable formulation is used for formulating a medicament for the treatment of hypoglycemia. In some embodiments, the stable formulation comprises glucagon or a salt thereof (e.g., glucagon acetate). In some embodiments, the stable formulation comprises glucagon and exenatide.

In some embodiments, the stable formulation is used for formulating a medicament for the treatment of diabetes. In some embodiments, the stable formulation comprises insulin. In some embodiments, the stable formulation comprises exenatide. In some embodiments, the stable formulation comprises pramlintide. In some embodiments, the stable formulation comprises insulin and pramlintide.

In additional embodiments, the formulations provided by the present invention may be used in certain diagnostic procedures. In particular such embodiments, a glucagon-containing formulation of the present invention can be administered to a mammal, such as a human or a veterinary animal, prior to, as an adjunct to, as a part of, or in conjunction with, one or more diagnostic procedures, thereby providing a method of diagnosing the disease or disorder in a patient suffering from or predisposed to the disease or disorder. Non-limiting examples of such diagnostic procedures in which a glucagon-containing formulation of the present invention may be suitably used include methods for diagnosing Alzheimer's Disease (see U.S. Pat. No. 4,727,041, incorporated herein by reference in its entirety) and growth hormone deficiency (see U.S. Pat. No. 5,065,747; see also Boguszewski, C. L., *Endocrine* 57: 361-363 (2017), and Yuen, K. C. J., *ISRN Endocrinology*, vol. 211, Article ID 608056, pp. 1-6 (2011), doi:10.5402/2011/608056; the disclosures of all of which are incorporated by reference herein in their entireties). Additional examples of such uses include in certain radiologic diagnostic procedures, particularly those used in diagnosing gastroenterologic conditions (non-limiting examples of which include abdominal obstructions, appendicitis, Barrett's esophagus, celiac disease, cancers, cirrhosis, Crohn's disease, diverticulitis, diverticulosis, ulcers, gallstones, gastric prolapse, gastritis, gastroesophageal reflux disease, hepatitis (A/B/C), hiatus hernia, inflammatory bowel disorder, hernia, irritable bowel syndrome, pancreatitis, perianal fissure, ulcerative colitis, and the like), during radiologic examinations of the gastrointestinal system to temporarily inhibit movement of the organs and connective tissues of the gastrointestinal tract in adult patients (see, e.g., product label for glucagon, lyophilized (NDC Code 63323-185-03), accessible at: https://dailymed.nlm.nih.gov/dailymed/drugInfo.cfm?setid=8c8acad6-44cc-43aa-966b-027e053be8f5; see also, *Glucagon in Gastroenterology*, J. Picazo, ed., Lancaster, England: MTP Press Ltd. (1979), especially Chapters 3-7, pp. 39-120; the disclosure of which is incorporated herein by reference). In such diagnostic methods, the glucagon-containing formulation of the invention is administered to the patient suffering from or predisposed to the disorder by any suitable method of introduction of such formulation into the body of the patient such as those described herein, e.g., intravenously at dosages of about 0.2 mg to about 0.75 mg about 1-10 minutes prior to the diagnostic test (e.g., the radiologic procedure), or intramuscularly or intradermally at dosages of about 1 mg to about 2 mg about 5-15 minutes prior to the diagnostic test (e.g., the radiologic procedure). Other suitable therapeutic and diagnostic methods of use of the formulations of the present invention will be readily familiar to the ordinarily skilled clinician or pharmacist based on the disclosure contained herein in view of information that is available in the art.

IV. Kits/Containers

Kits are also contemplated as being used in certain aspects of the present invention. For instance, a formulation of the present invention can be included within a kit, which can include a container. In one aspect, for instance, the formulation can be comprised within a container that is ready to administer to or be incorporated into a device configured to administer to a subject without having to reconstitute or dilute the formulation. That is, the formulation to be administered can be stored in the container and be readily used as needed. The container can be a device. The device can be a syringe (e.g., pre-filled syringe), a pen injection device, an auto-injector device, a device that can pump or administer the formulation (e.g., automatic or non-automatic external pumps (e.g. patch pumps, or pumps requiring an external infusion set), implantable pumps, etc.) or a perfusion bag. Suitable pen/auto-injector devices include, but are not limited to, those pen/auto-injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like. Suitable infusion sets include, but are not limited to, those manufactured/distributed/sold by Tandem Diabetes Care, Inc., Medtronic, Disetronic, YpsoMed Ag, Unomedical A/S and the like.

EXAMPLES

Some embodiments of the present disclosure will be described in greater detail by way of specific examples. The following examples are offered for illustrative purposes and are not intended to limit any present invention in any manner. For example, those of skill in the art will readily recognize a variety of noncritical parameters which can be changed or modified, without undue experimentation, to yield essentially the same results.

Example 1: Preparation of Sustained Release Glucagon Formulations

Previous reports of the preparation of sustained release glucagon formulations have relied upon the preparation of aqueous zinc-glucagon suspensions and crystallization of the Zn-glucagon complex; upon rehydration, such Zn-glucagon suspensions demonstrated sustained release of glucagon (see Trading, F. et al., *Eur. J. Pharmacol.* 7:206-210 (1969)). However, such aqueous suspensions of glucagon must be prepared immediately before therapeutic use, as resuspension of glucagon in an aqueous solution leads to rapid hydrolysis and loss of activity of the glucagon, a problem that can be overcome by dissolving the glucagon in an aprotic solvent system such as DMSO which enhances long-term storage stability of the glucagon solution (see, e.g., U.S. Pat. Nos. 9,339,545 and 10,485,850, the disclosures of which are incorporated herein in their entireties). Thus, it was desirable to evaluate the ability to prepare sustained release (SR) formulations of glucagon that are also storage stable in solution.

In an initial study of the stability of such formulations, glucagon formulations were prepared at 5 mg/mL or 10 mg/mL in DMSO in glass vials, containing varying concentrations of a divalent zinc compound (zinc chloride, zinc acetate, or zinc sulfate) also present in the solution. All formulations also had the following components: 5.5% (w/v) trehalose dihydrate and 2.9% (w/v) mannitol. The following exemplary formulations were prepared ("Control" is a commercially available, non-SR, liquid glucagon formulation (GVOKE®, Xeris Pharmaceuticals, Inc., Chicago, IL):

TABLE 1

Exemplary SR Glucagon Formulations.

| Formulation | Glucagon Concentration | Zinc compound; concentration | Zinc/Glucagon Ratio |
|---|---|---|---|
| Control | 5 mg/mL | None (3.2 mM $H_2SO_4$) | N/A |
| A-1 | 10 mg/mL | Zinc acetate; 11.5 mM | 4:1 |
| A-2 | 10 mg/mL | Zinc acetate; 23 mM | 8:1 |
| A-3 | 5 mg/mL | Zinc acetate; 1.4 mM | 1:1 |
| A-4 | 5 mg/mL | Zinc acetate; 5.7 mM | 4:1 |
| A-5 | 5 mg/mL | Zinc acetate; 11. mM | 8:1 |
| A-6 | 5 mg/mL | Zinc acetate; 23 mM | 16:1 |
| B-1 | 10 mg/mL | Zinc chloride; 11.5 mM | 4:1 |
| B-2 | 10 mg/mL | Zinc chloride; 23 mM | 8:1 |
| C-1 | 10 mg/mL | Zinc sulfate; 11.5 mM | 4:1 |
| C-2 | 10 mg/mL | Zinc sulfate; 23 mM | 8:1 |

Divalent zinc compounds were selected based on compatibility with the glucagon formulation and suitability for subcutaneous use. Physicochemical stability of the formulations was analyzed via visual analysis and reverse phase UHPLC (RP-UPHLC) after storage at various temperatures (−20° C., 5° C., 25° C./60% relative humidity, or 40° C./75% relative humidity) in stability test chambers. After up to 6 months in storage, samples of each formulation were examined visually for the presence of discoloration, gelation or aggregation of the contents of the vial and were photographed. For RP-UPHLC analysis, a gradient method was developed based on 1% trifluoracetic acid (TFA) and acetonitrile and a Waters ACQUITY UPLC® Peptide CSH C18, 100 mm×2.1 mm, 1.7 μm, 130 Å column. Detection was at 280 nm; flow Rate was 0.55 mL/min; column temperature was 60° C.; injection quantity was 25 μg of glucagon. Purity of glucagon in each formulation was then determined by assessing the area of main peak (non-degraded glucagon) as a percent of the main peak in the starting material (time 0) for that formulation.

FIG. 1 shows exemplary photographs of two of the exemplary SR glucagon formulations described in Table 1—formulation A-1 (FIG. 1A) and formulation A-2 (FIG. 1B)—photographed immediately after preparation. As seen in FIG. 1, for these formulations no discoloration, gelation or aggregation were visually observed in the vials at storage time T=0. Similar results were obtained for the other formulations listed in Table 1 (data not shown).

Upon storage for up to six months at varying temperatures, certain of the SR formulations performed better than others in terms of storage stability, assessed visually for discoloration and aggregation/fibril formation (fibrillation). These results are shown in FIGS. 2-5.

In samples stored at −20° C. for 6 months (FIG. 2), the following visual results for discoloration (FIG. 2A) and fibrillation (FIG. 2B) were obtained:

| Sample | Appearance |
|---|---|
| Control | Clear, colorless solution. Free of visible particulates |
| A-1 | Somewhat cloudy, white solution. Extent of opacity increases with decreasing storage temperature. |
| A-2 | Somewhat cloudy, white solution. Extent of opacity increases with decreasing storage temperature. |
| B-1 | Clear, colorless solution. Free of visible particulates |
| B-2 | Clear, colorless solution. Free of visible particulates |
| C-1 | Clear, colorless solution. Free of visible particulates |
| C-2 | Clear, colorless solution. Free of visible particulates |

In samples stored at 5° C. for 6 months (FIG. 3), the following visual results for discoloration (FIG. 3A) and fibrillation (FIG. 3B) were obtained:

| Sample | Appearance |
|---|---|
| Control | Clear, colorless solution. Free of visible particulates |
| A-1 | Somewhat cloudy, white solution. Extent of opacity increases with decreasing storage temperature. |
| A-2 | Somewhat cloudy, white solution. Extent of opacity increases with decreasing storage temperature. |
| B-1 | Clear, colorless solution. Clear gel precipitate observed above the liquid surface, which dissolved once reaching room temperature. |
| B-2 | Somewhat cloudy solution. Clear gel precipitate observed above the liquid surface. Both cloudiness and precipitate dissolved once reaching room temperature. |
| C-1 | Somewhat cloudy solution. Clear gel precipitate observed above the liquid surface. Both cloudiness and precipitate dissolved once reaching room temperature. |
| C-2 | Clear, colorless solution. Free of visible particulates |

In samples stored at 25° C. for 6 months (FIG. 4), the following visual results for discoloration (FIG. 4A) and fibrillation (FIG. 4B) were obtained:

| Sample | Appearance |
|---|---|
| Control | Clear, colorless solution. Free of visible particulates |
| A-1 | Somewhat cloudy, white solution. Extent of opacity increases with decreasing storage temperature. |
| A-2 | Somewhat cloudy, white solution. Extent of opacity increases with decreasing storage temperature. |
| B-1 | Clear, colorless solution. Clear gel precipitate observed above the liquid surface. |
| B-2 | Clear, colorless solution. Free of visible particulates |
| C-1 | Clear, colorless solution. Free of visible particulates |
| C-2 | Clear, colorless solution. Free of visible particulates |

In samples stored at 40° C./75% relative humidity for 6 months (FIG. 5), the following visual results for discoloration (FIG. 5A) and fibrillation (FIG. 5B) were obtained:

| Sample | Appearance |
|---|---|
| Control | Clear, colorless solution. Free of visible particulates |
| A-1 | Somewhat cloudy, white solution. Extent of opacity increases with decreasing storage temperature. |
| A-2 | Somewhat cloudy, white solution. Extent of opacity increases with decreasing storage temperature. |
| B-1 | Clear, colorless solution. Clear gel precipitate observed above the liquid surface. |
| B-2 | Clear, colorless solution. Free of visible particulates |
| C-1 | Clear, colorless solution. Free of visible particulates |
| C-2 | Clear, colorless solution. Free of visible particulates |

More sensitive analyses of the stability of certain of these formulations (specifically, those stored for 6 months at 25° C.; FIG. 4), via RP-UHPLC, revealed similar results as shown in Table 2.

TABLE 2

Purity of Glucagon Formulations Stored × 6 months at 25° C., by RP-UHPLC

| Formulation | Storage Time (months) | | | | |
|---|---|---|---|---|---|
| | 0 | 1 | 2 | 3 | 6 |
| Control | 100 | 100 | 99 | 99 | 97 |
| A-1 | 100 | 99 | 96 | 97 | 92 |
| A-2 | 100 | 99 | 96 | 97 | 91 |
| B-1 | 100 | 100 | 98 | 99 | 96 |
| B-2 | 100 | 100 | 99 | 99 | 96 |
| C-1 | 100 | 99 | 98 | 98 | 95 |
| C-2 | 100 | 99 | 98 | 98 | 95 |

Figure 7C:
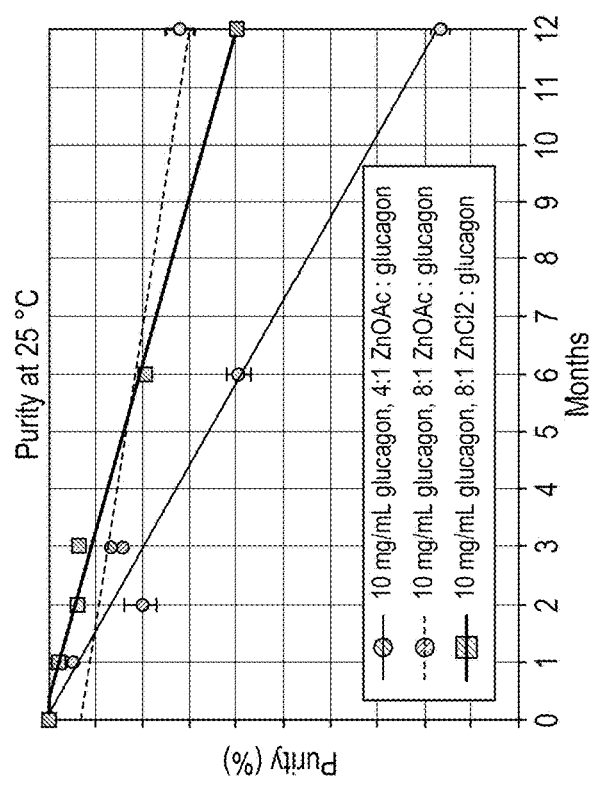
FIGS. 7A-7D are a series of photographs and line graphs demonstrating the stability of SR glucagon formulations of the invention. Samples were evaluated for purity via RP-UHPLC and were photographed, after storage for 12 months at either 5° C.
Figure 7D:
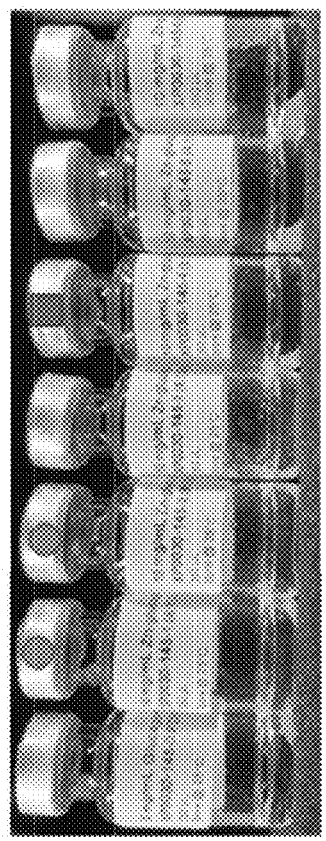
Figure 7A:
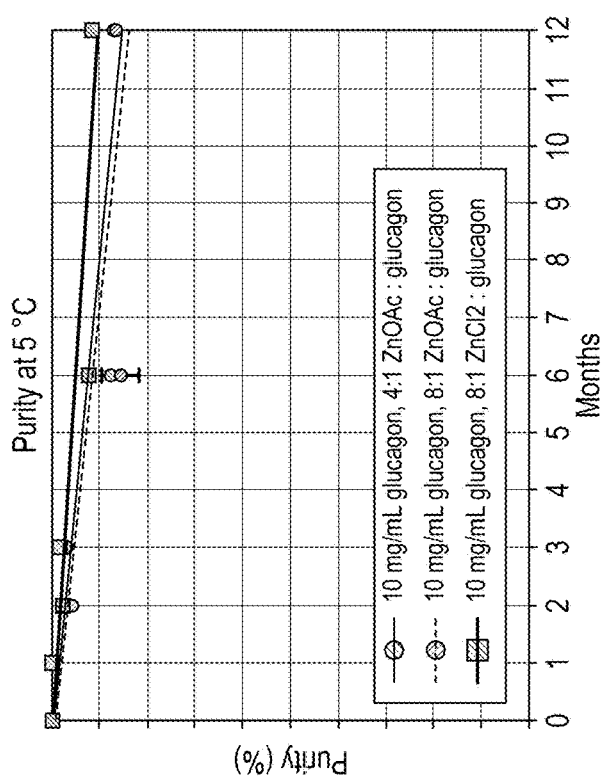
Figure 7B:

These studies were extended to twelve months storage of these same formulation samples, stored at 5° C. and 25° C. Results are shown in FIG. 7. As seen in FIGS. 7A and 7B, storage of the samples at 5° C. for up to 12 months resulted in very little degradation or fibrillation of the formulations; all formulations demonstrated 98-99% purity even after 12 months of storage when evaluated by RP-UHPLC. Storage of the formulation samples for 12 months at 25° C. (FIGS. 7C and 7D) indicated that the initial slight degradation seen in the 4:1 glucagon:zinc acetate formulation continued from month 6 to month 12, until about 84% purity was observed in this sample. In contrast, the 8:1 glucagon:zinc acetate and the 8:1 glucagon:zinc chloride formulations continued to degrade but at a much slower rate, retaining about 92-94% of their initial purity after 12 months of storage at 25° C.

Together, these results demonstrate that all of the zinc-containing SR glucagon formulations demonstrate long-term room temperature stability for at least three months, with the formulations containing zinc chloride (B-1, B-2) and zinc sulfate (C-1 and C-2) demonstrating longer-term stability at 25° C.-40° C. (up to at least 6 months) compared to the zinc acetate-containing formulations (A-1, A-2) which were somewhat less stable when stored at 25° C.-40° C. for 6 months. Similar results were observed at longer storage times, with all formulations demonstrating excellent long-term storage (at least 12 months) after storage at 5° C., with slightly lower stability at longer-term (12 months) storage at 25° C., with the 8:1 glucagon/zinc acetate formulation showing the highest long-term stability upon storage at 25° C. The 25° C.-40° C. storage stability of the zinc chloride and zinc sulfate formulations approximated those seen with the control formulation, a commercially available storage stable liquid glucagon formulation.

Example 2: Evaluation of Storage Stable SR Glucagon Formulations in Pre-Clinical Studies Based on the results described above, it was of interest to examine the initial pharmacokinetics (PK) of the storage stable SR glucagon formulations described in Example 1, in pre-clinical studies in laboratory animals. Jugular vein-cannulated, Sprague-Dawley rats (n=3/group) were all dosed subcutaneously with test formulations via a needle and syringe into the tented skin between the scapulae. Dose volumes were adjusted for the weight of the animal on the morning of dose administration. The storage stable SR glucagon solutions were given as 60 μL to 250 μL injections of 2 mg/kg to 8 mg/kg. A formulation similar to a commercially available non-SR glucagon rescue product (GVOKE®; Xeris Pharmaceuticals, Chicago, IL) was used as a control. Blood samples were collected from each animal into $K_2$EDTA protease inhibitor P800 blood tubes at pre-dose, and at 0.25, 0.5, 1, 1.5, 2, 4, 6, 12, 24 and 48 hours post-dose. Pharmacokinetic parameters were analyzed for the three treatment groups plus the control. Plasma glucagon was assayed via LC-MS at AltaSciences (Laval, Quebec, Canada). A non-compartmental PK analysis was performed for each animal. Cmax and Tmax were computed from observed data, while Area-under-the-curve (AUC) estimates were calculated using a linear trapezoid method:

$$AUC = \tfrac{1}{2}(C_1+C_2)(t_2-t_1)$$

Elimination half-life (t½) was calculated as follows:

$$t1/2 = \frac{0.693}{k} \text{ and } k = \frac{CL}{V_d}$$

k=elimination rate constant
CL=clearance
$V_d$=volume of distribution

Figure 6:
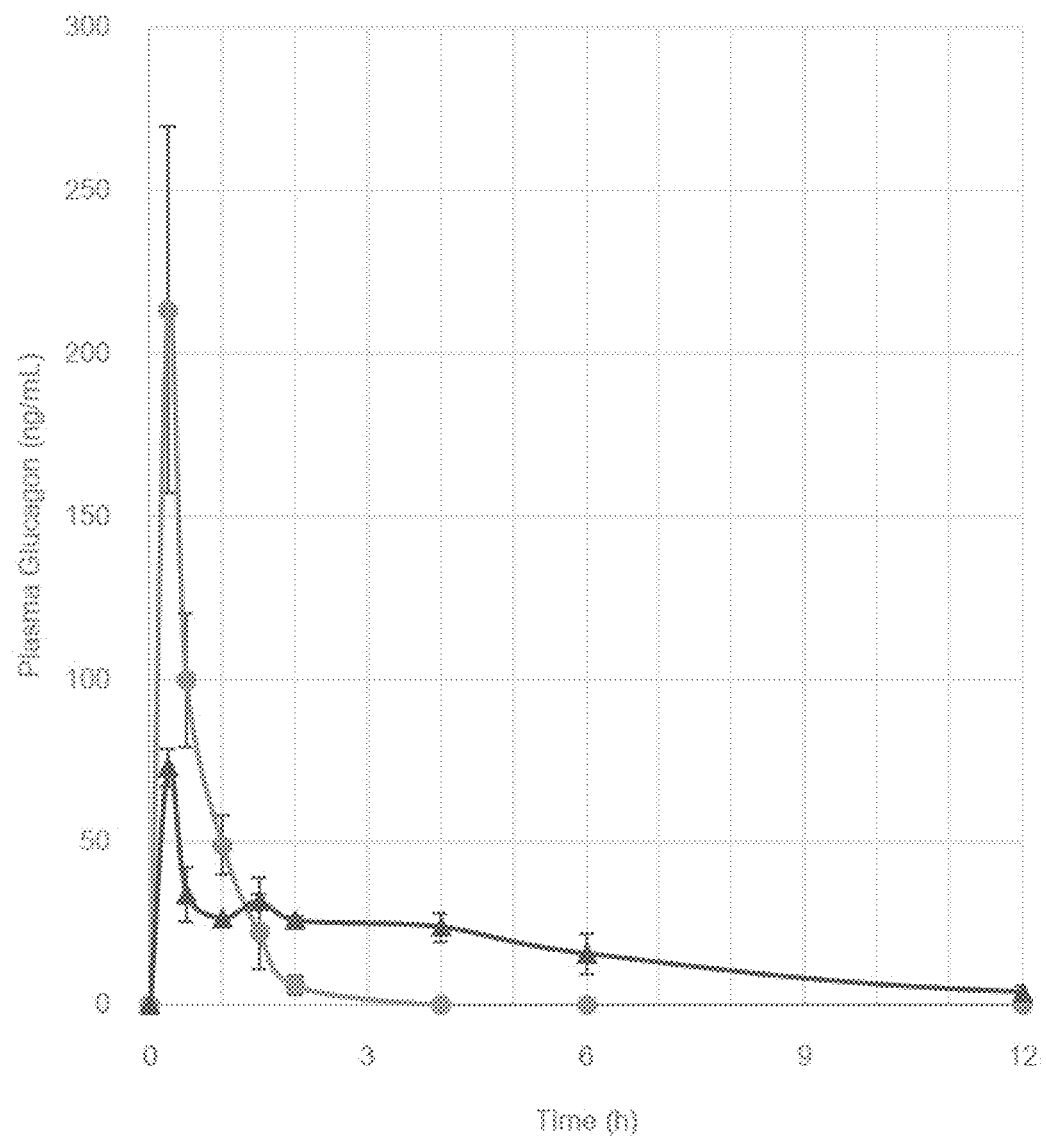
FIG. 6 is a line graph demonstrating comparative pharmacokinetic (PK) studies of an exemplary SR glucagon formulation of the invention compared to an immediate-release control glucagon formulation. Graph shows mean±SD (n=3) plasma glucagon levels and half-life of select formulations in a rat PK study. ●: control (commercial immediate-release glucagon formulation); ▲: SR glucagon formulation (formulation A-1; see Table 1 in Example 1).

Exemplary PK results for one of the SR glucagon formulations (A-1) are shown in FIG. 6.

As seen in FIG. 6, there was an extension of the elimination half-life of glucagon from approximately 0.3 hours for the non-SR control to at least 6.1 hours for the SR (zinc-containing) glucagon formulations. Moreover, the SR formulations resulted in minimal burst release of glucagon (Cmax=73 ng/mL) and demonstrated a relatively flat and temporally extended release profile, compared to the non-SR immediate release control formulations (Cmax=214 ng/mL). Thus, storage stable SR glucagon formulations of the present invention are able to maximize the time that blood glucagon levels remain within the therapeutic window after administration, unlike the control, a commercially available rescue product which is intended to rapidly bring up glucagon levels in response to a severe hypoglycemic event These pharmacokinetic studies were then expanded with additional formulations, including those described in Example 1, to examine whether or not these formulations could be suitable for producing a SR glucagon formulation that could be therapeutically beneficial with administration to subjects only once per day. Formulations were prepared as shown in Table 3:

TABLE 3

Zinc-Glucagon Formulations Prepared for Animal PK Studies.

| Group | Description | Composition | Dose (mg/kg) |
|---|---|---|---|
| Group 1 (Control) | GVOKE ® glucagon (immediate release) | 5 mg/mL glucagon, 5.5% trehalose DH, 2.9% mannitol, 3.2 mM $H_2SO_4$. DMSO | 2 |
| Group 2 | 5 mg/mL SR glucagon (1:1 Zn:glucagon) | 5 mg/mL glucagon, 5.5% trehalose DH, 2.9% mannitol, 1.4 mM zinc acetate, DMSO | 2 |

TABLE 3-continued

Zinc-Glucagon Formulations Prepared for Animal PK Studies.

| Group | Description | Composition | Dose (mg/kg) |
|---|---|---|---|
| Group 3 | 5 mg/mL SR glucagon (4:1 Zn:glucagon) | 5 mg/mL glucagon, 5.5% trehalose DH, 2.9% mannitol, 5.7 mM zinc acetate, DMSO | 2 |
| Group 4 | 5 mg/mL SR glucagon (8:1 Zn:glucagon) | 5 mg/mL glucagon, 5.5% trehalose DH, 2.9% mannitol, 11.5 mM zinc acetate, DMSO | 2 |
| Group 5 | 5 mg/mL SR glucagon (16:1 Zn:glucagon) | 5 mg/mL glucagon, 5.5% trehalose DH, 2.9% mannitol, 23 mM zinc acetate, DMSO | 2 |
| Group 6 | 10 mg/mL SR glucagon (4:1 Zn:glucagon) | 10 mg/mL glucagon, 5.5% trehalose DH, 2.9% mannitol, 11.5 mM zinc acetate, DMSO | 2 |
| Group 7 | 10 mg/mL SR glucagon (4:1 Zn:glucagon) | 10 mg/mL glucagon, 5.5% trehalose DH, 2.9% mannitol, 11.5 mM zinc acetate, DMSO | 4 |
| Group 8 | 10 mg/mL SR glucagon (4:1 Zn:glucagon) | 10 mg/mL glucagon, 5.5% trehalose DH, 2.9% mannitol, 11.5 mM zinc acetate, DMSO | 8 |
| Group 9 | 10 mg/mL SR glucagon (8:1 Zn:glucagon) | 10 mg/mL glucagon, 5.5% trehalose DH, 2.9% mannitol, 23 mM zinc acetate, DMSO | 2 |

Figure 8B:
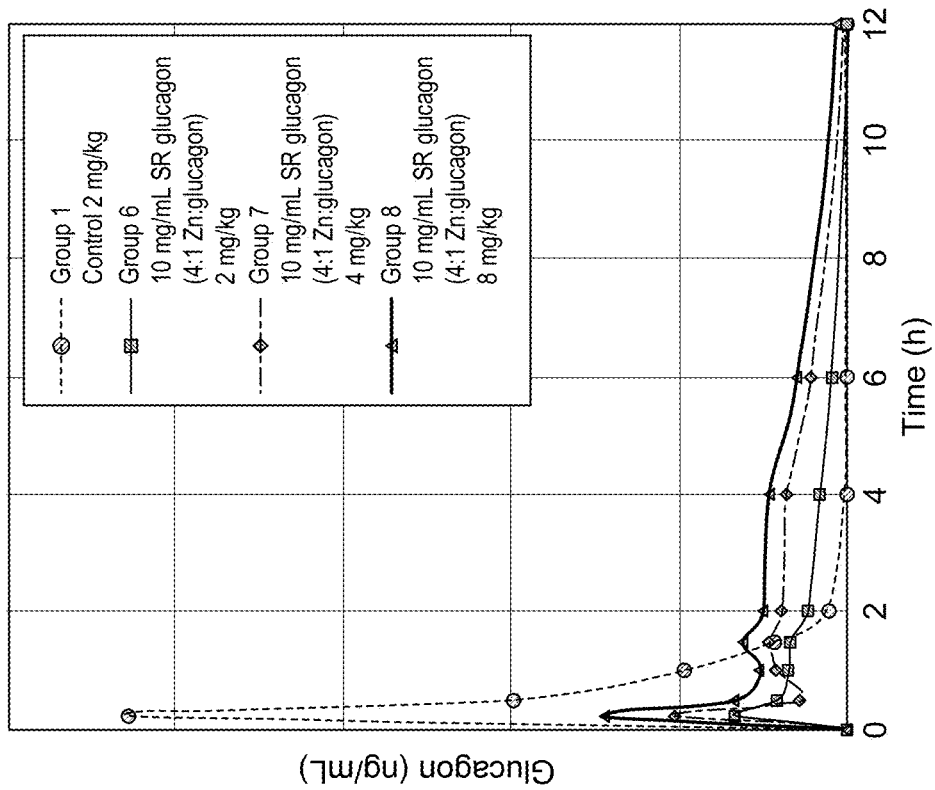
FIGS. 8A-8B are a pair of line graphs demonstrating comparative pharmacokinetic (PK) studies of certain SR glucagon formulations of the invention compared to an immediate-release control glucagon formulation. Graph shows mean±SD (n=3) plasma glucagon levels and half-life of select formulations in a rat PK study.
Figure 8A:
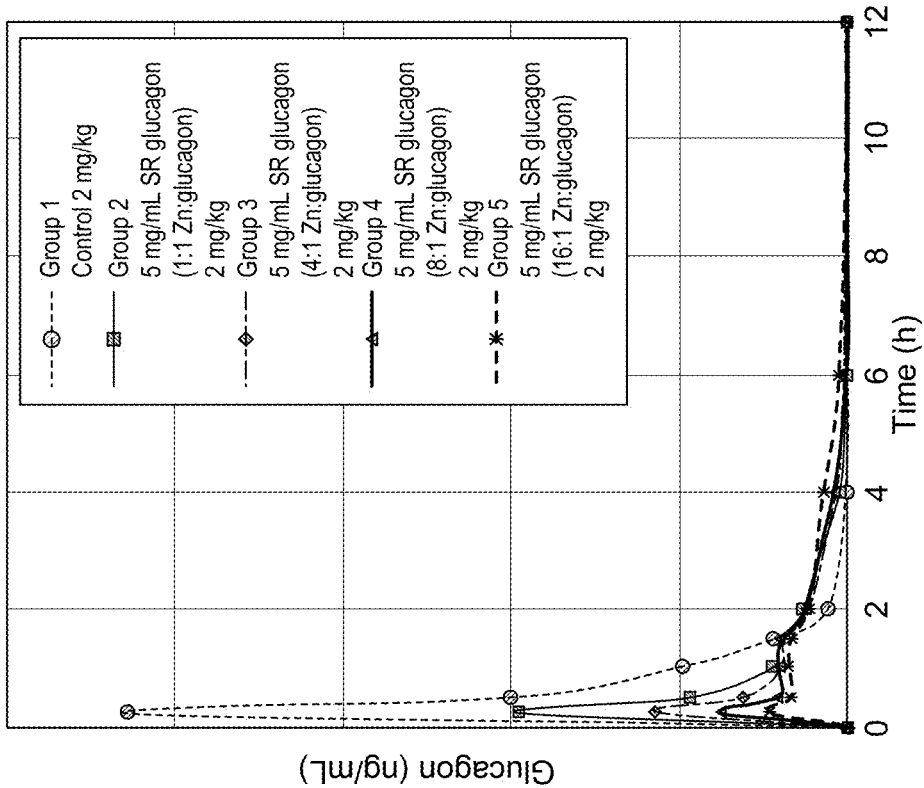

These formulations were then administered to rats subcutaneously as described elsewhere herein and the plasma glucose levels were assessed in treated animals over the course of 12 hours. Results are shown in FIG. 8. As seen in both FIG. 8A and FIG. 8B, the control immediate-release GVOKE® (glucagon injection) formulation demonstrated the expected kinetics with a high Cmax and relatively short plasma half-life, compared to the SR (zinc-containing) glucagon formulations. The specific PK values for each of these formulations are shown in Table 4:

TABLE 4

Pharmacokinetic Results of Once-Per-Day SR Glucagon Formulations.

| Group | Description | Ratio Zn:Glucagon | Dose (mg/kg) | Cmax (ng/mL) | AUC | Tmax (min) | Mean T ½ (min) |
|---|---|---|---|---|---|---|---|
| Control | GVOKE ® glucagon | N/A | 2 | 214 ± 56 | 134 ± 6 | 15 | 20 |
| Group 2 | 5 mg/mL SR glucagon | 1 | 2 | 98 ± 26 | 88 ± 24 | 15 | 93 |
| Group 3 | 5 mg/mL SR glucagon | 4 | 2 | 57 ± 11 | 69 ± 7 | 15 | 65 |
| Group 4 | 5 mg/mL SR glucagon | 8 | 2 | 38 ± 2 | 57 ± 6 | 15 | 69 |
| Group 5 | 5 mg/mL SR glucagon | 16 | 2 | 23 ± 6 | 69 ± 24 | 15 | 77 |
| Group 6 | 10 mg/mL SR glucagon | 4 | 2 | 34 ± 14 | 88 ± 8 | 15 | 102 |
| Group 7 | | | 4 | 52 ± 13 | 168 ± 32 | 15 | 312 |
| Group 8 | | | 8 | 73 ± 6 | 249 ± 43 | 15 | 366 |
| Group 9 | 10 mg/mL SR glucagon | 8 | 2 | 27 ± 2 | 68 ± 32 | 15 | 125 |

These results indicate that it is possible to prepare sustained release glucagon formulations that provide an optimal and therapeutic plasma glucagon concentrations over extended time periods, even with administration only once per day. In particular, formulations with an increased zinc:glucagon ratio demonstrated a reduction in initial burst release of glucagon (i.e., a lower Cmax) and slower decay of the plasma glucagon levels over time. Moreover, at a given ratio of zinc:glucagon, administration of a higher dose of the formulation or a higher concentration of glucagon in the formulation both resulted in higher plasma glucagon activity (i.e., higher AUC and $T_{1/2}$).

Together with those of Example 1, these results indicate that it is possible to produce storage stable SR glucagon formulations, which have not previously been demonstrated or contemplated. Such storage stable SR glucagon formulations can be used not only in an emergency rescue scenario for patients suffering from acute severe hypoglycemia, but also potentially in non-emergency treatment and prevention approaches to managing blood glucose levels, for example for use before sleep, exercise, or in circumstances where the patient may be unaware of a decline in blood glucose, potentially over a prolonged period of time. Moreover, these results indicate that it is also possible to prepare glucagon formulations that can be advantageously administered once per day to a patient, eliminating the need to use glucagon only in rescue situations and potentially providing for better management of a patient's blood glucose levels than is currently available.

Example 3: Preparation of Once-Weekly Glucagon Formulations

Having demonstrated the ability to produce sustained release (SR) glucagon formulations, it was of interest to the inventors to determine whether or not the same principles could be applied to prepare long-acting ("LA") glucagon formulations such as formulations that might be administered only once per week to a patient in need of blood glucose management. Ideally, such formulations would provide for subcutaneous or intradermal administration, minimal initial burst release of glucagon, and near linear release of glucagon into the bloodstream over a period of at least a week without the need for additional administration of glucagon over that time period. Such formulations would be particularly useful to patients suffering from Type 2 diabetes, as an example, and could result not only in better self-management of blood glucose by these patients but also provide the potential for a reduction in body weight and improved HbA1c levels in such patients.

Figure 9A:
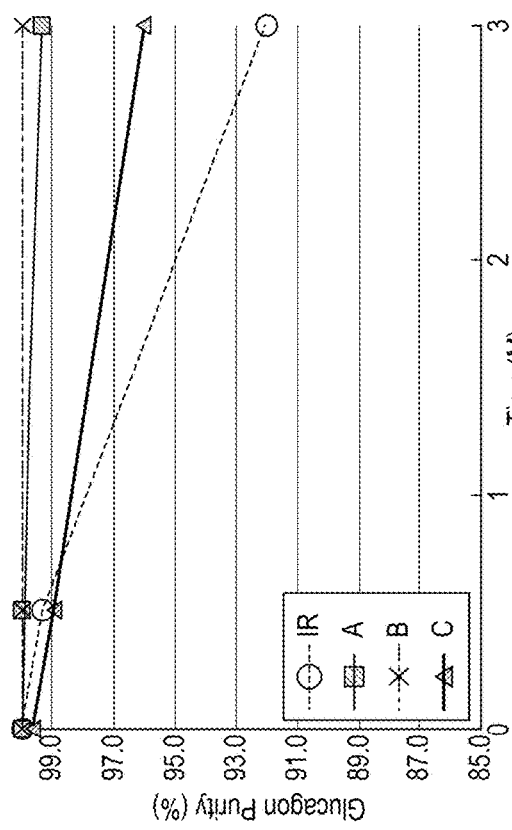
FIGS. 9A-9D are a series of line graphs demonstrating the stability of long-acting ("LA") glucagon formulations of the invention. Formulations were prepared as described in Example 3 hereinbelow and were evaluated for purity via RP-UHPLC after storage for 3 months at −20° C.
Figure 9B:
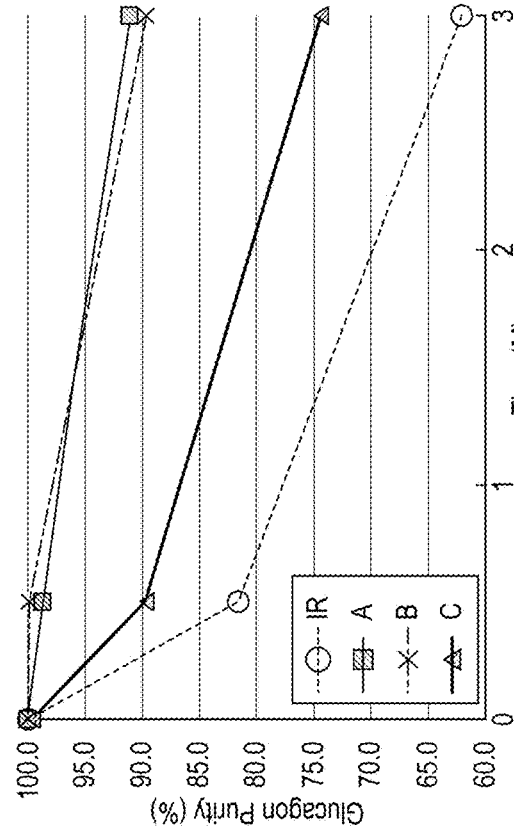
Figure 9C:
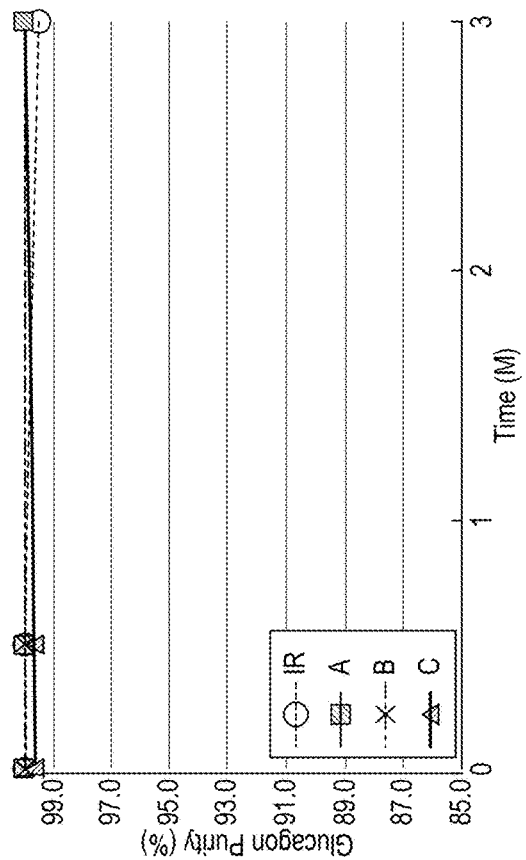
Figure 9D:
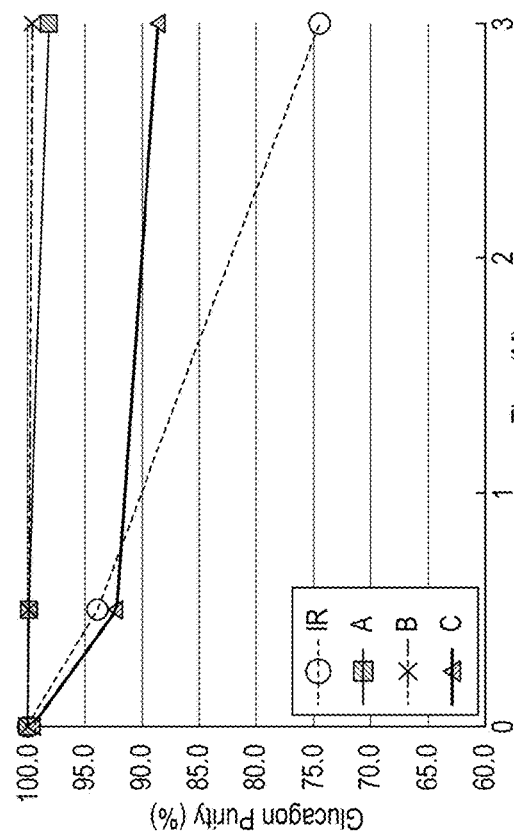

To produce these formulations, glucagon was formulated using certain polymers that provide for slow-release of a variety of peptide therapeutics. In particular, poly-lactide-co-glycolides (PLGAs) were explored as suitable carriers for producing such LA glucagon formulations. Two PLGA polymers were examined: RESOMER® RG502 (poly(D,L-lactide-co-glycolide) 50:50, 0.16-0.24 dl/g (MW~7-17 kD) which has an ester end group, and RESOMER® RG502H ((poly(D,L-lactide-co-glycolide) 50:50, 0.16-0.24 dl/g (MW~7-17 kD) which has an acid end group; both were obtained from Evonik (Parsippany, NJ). Various formulations of glucagon in DMSO (100 mg/ml) were prepared as described in Examples 1 and 2, and PLGAs in the presence or absence of trehalose (5% w/v) were added to the formulations. Samples of each formulation were then stored for three months at −20° C., 5° C., 25° C. and 40° C., and the samples evaluated for storage stability as described in the preceding Examples. Results are shown in FIG. 9. As was observed in the preceding Examples, all of the formulations including the immediate-release GVOKE® control formulation demonstrated nearly no degradation over three months when stored at −20° C. (FIG. 9A). In contrast, while the immediate-release formulation degraded significantly at 5° C. (FIG. 9B), 25° C. (FIG. 9C) and 40° C. (FIG. 9D), the SR formulations that had been formulated with PLGA showed much better storage stability, with two of the formulations (containing either ester-terminated PLGA or PLGA and trehalose) showing enhanced long-term storage stability even at 40° C. (FIG. 9D). These results indicate that the inclusion of PLGA in the formulations did not reduce, and to the contrary appeared to enhance, the storage stability of DMSO-glucagon formulations.

Figure 10:
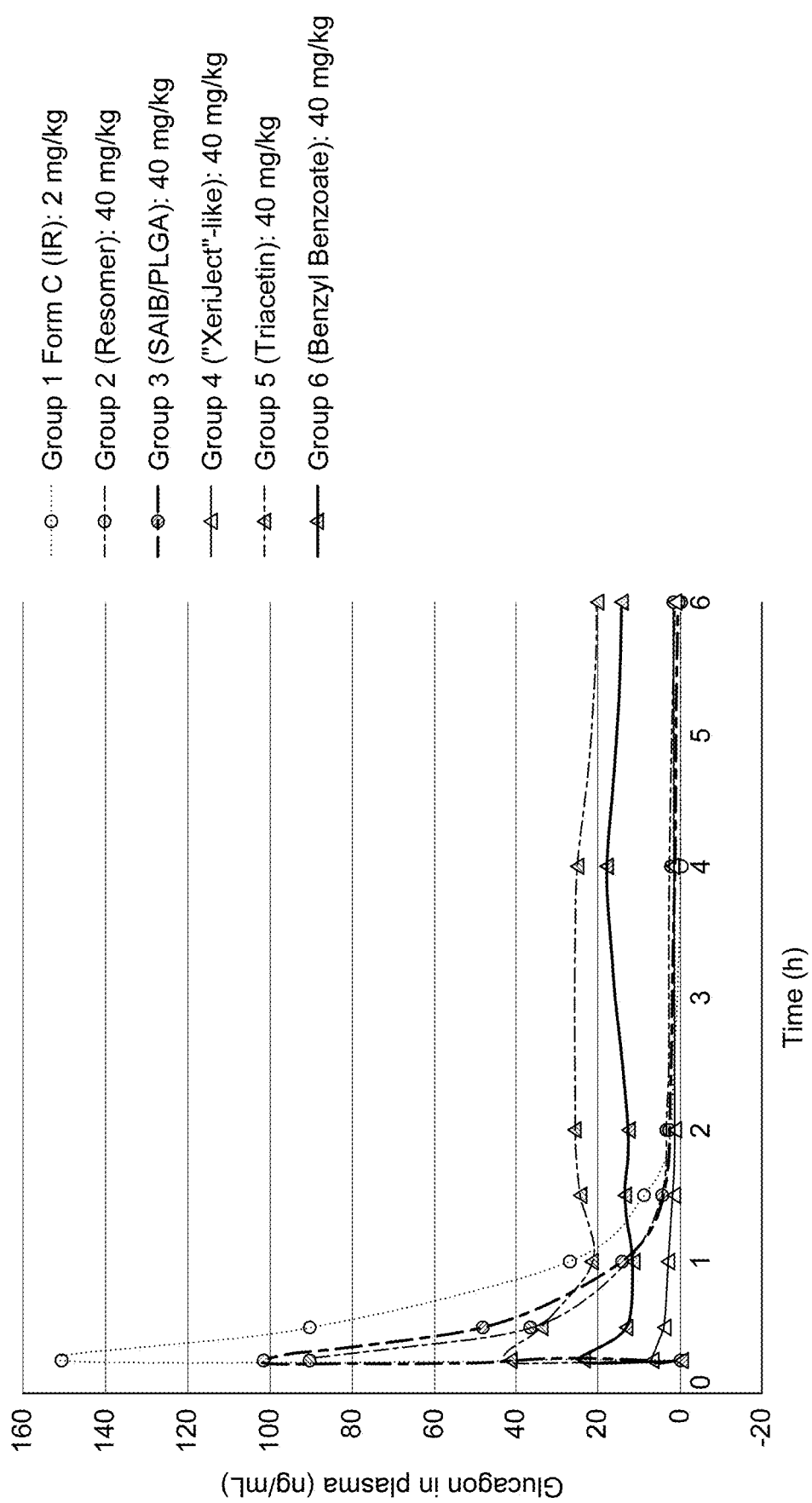
FIG. 10 is a line graph demonstrating comparative pharmacokinetic (PK) studies of certain LA glucagon formulations of the invention compared to an immediate-release control glucagon formulation. Graph shows mean±SD (n=3) plasma glucagon levels and half-life of select formulations in a rat PK study. Group 1: immediate-release GVOKE® glucagon formulation; Group 2: Resomer® RG502 PLGA glucagon formulation; Group 3: Resomer RG502 PLGA and Sucrose acetoisobutyrate (SAIB) glucagon formulation; Group 4: paste-like high-concentration Xeriject™ glucagon formulation (Xeris Pharmaceuticals, Chicago, IL) (see U.S. Pat. Nos. 8,110,209, 8,790,679 and 9,314,424, which are incorporated herein by reference in their entireties); Group 5: glucagon formulation comprising triacetin; group 6: glucagon formulation comprising benzyl benzoate.

Next, the pharmacokinetics of these PLGA-containing formulations when administered to test animals (male SD rats) were examined using the methods described in Example 2 above. As shown in FIG. 10, the PLGA-containing formulations produced in these initial studies did not provide the desired pharmacokinetics. While a lower Cmax was observed in two PLGA-containing formulations, neither of these formulations provided the longer-term plasma glucagon formulations that were the goal of such formulations.

Figure 11A:
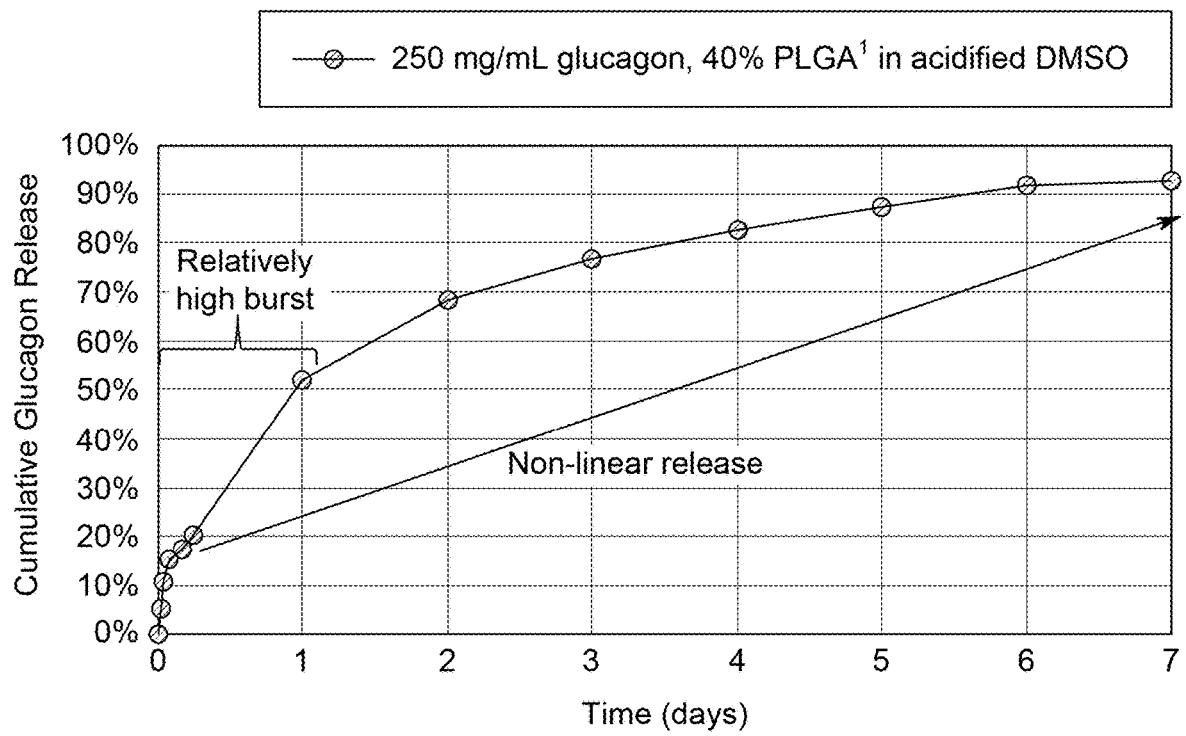
FIGS. 11A-11B are a pair of line graphs demonstrating comparative release kinetics in an in vitro assay system of certain LA glucagon formulations of the invention. Graphs show mean±SD (n=3) glucagon amounts in aqueous release media over time.
Figure 11B:
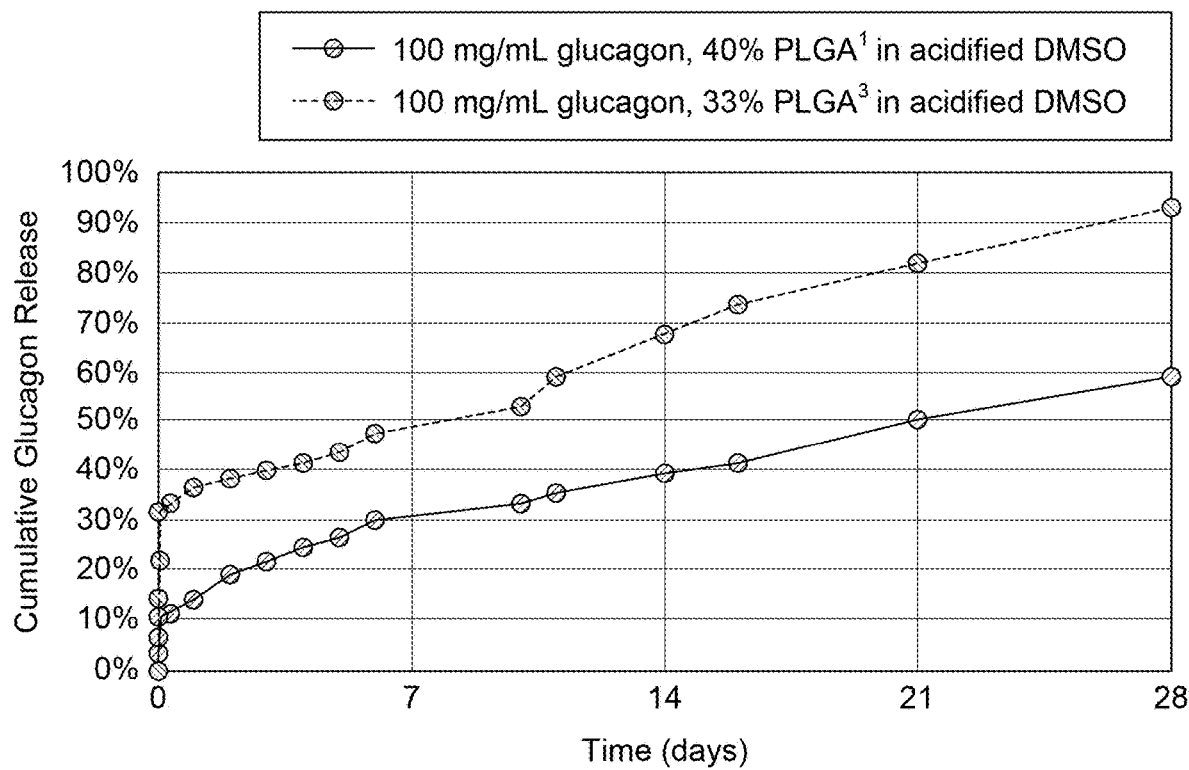

To attempt to optimize the formulations and provide the possibility of producing LA glucagon formulations, an in vitro release assay was used to examine the release kinetics of test formulations without having to sacrifice animals during the formulation development. In these experiments, test glucagon formulations were introduced into an aqueous release medium (PBS) in test containers incubated at 37° C., and samples were taken from the aqueous medium and tested for glucagon concentration over time. Results of an example of such studies are shown in FIG. 11. A formulation comprising 250 mg/mL glucagon and 40% Resomer® RG502 in acidified DMSO demonstrated a relatively high initial burst release and non-linear release of glucagon over a period of 7 days (FIG. 11A). In contrast, formulations comprising 100 mg/mL glucagon and 40% Resomer RG502 or 33% Resomer RG502H demonstrated near linear release with a low initial burst release of glucagon (FIG. 11B), but these formulations had a much longer than desired release duration (over a month required to release the full dose of glucagon).

Figure 12:
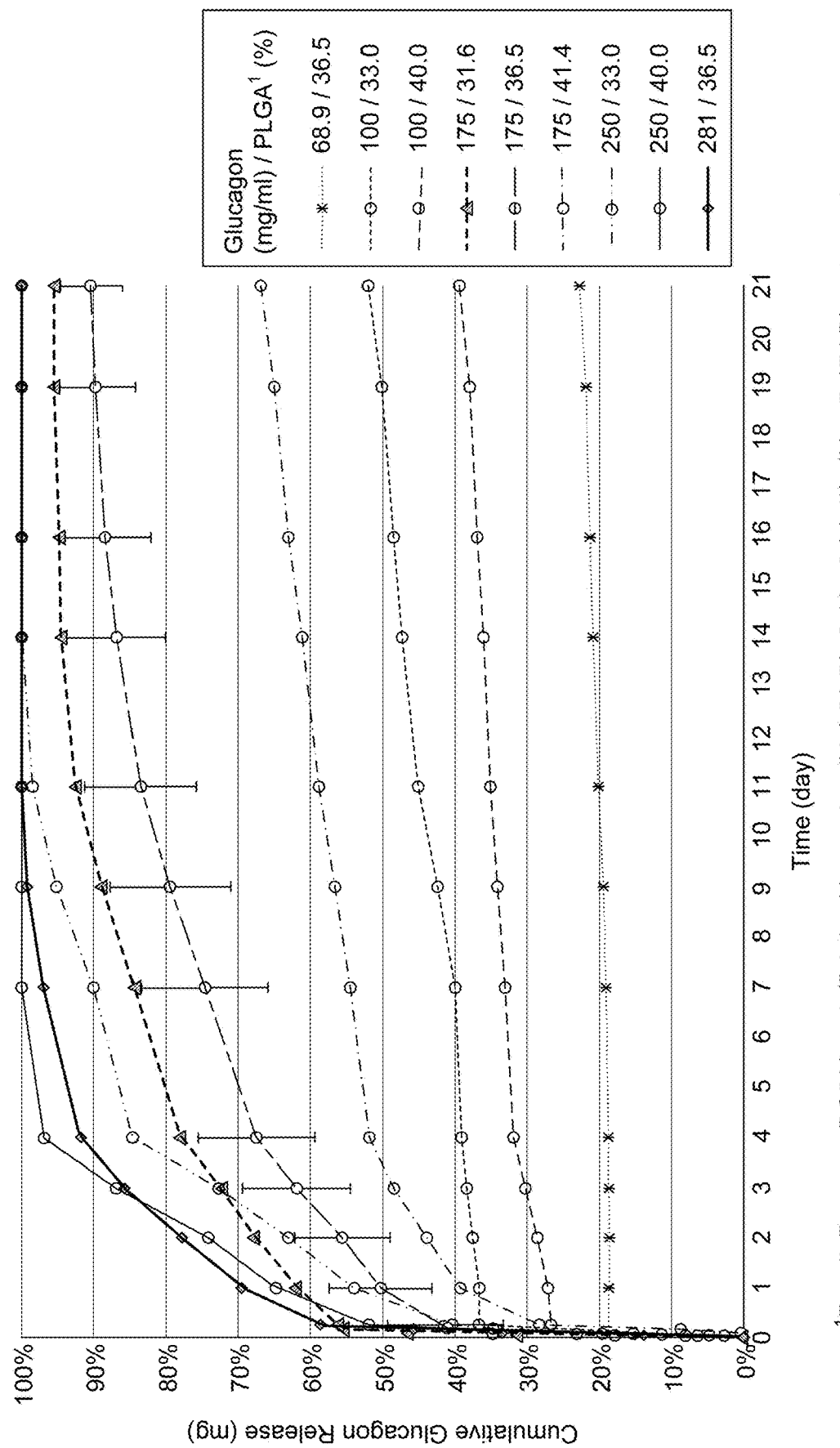
FIG. 12 is a line graph demonstrating comparative release kinetics in an in vitro assay system of certain LA glucagon formulations of the invention. Graphs show mean±SD (n=3) glucagon amounts in aqueous release media over time. Formulation components, and particularly the glucagon:PLGA ratios, are as shown on the right side of the graph.

These initial results were then used to optimize the formulation of glucagon in PLGA, to attempt to result in formulations that would provide optimal release characteristics within a suitable length of time (e.g., 1-2 weeks). Nine formulations were prepared using the Resomer RG502 (ester-terminated) PLGA and varying concentrations of glucagon and evaluated in the in vitro assay described above. Results of these studies are shown in FIG. 12. As seen in this figure, formulations containing 250 mg/mL glucagon and either 33% or 40% PLGA, as well as a formulation comprising 281 mg/mL glucagon and 36.5% PLGA, demonstrated a relatively low initial burst (Cmax), followed by sustained release over time and complete release of the glucagon in the formulation achieved within about 10-11 days. These results indicate that it is possible to produce LA glucagon formulations that are characterized by a low initial burst release of glucagon with extended release over time and complete release of the glucagon from the injected formulation into the bloodstream within less than two weeks.

All of the compositions and/or methods disclosed and claimed herein can be made and executed without undue experimentation in light of the present disclosure. While the compositions and methods of this disclosure have been described in terms of some embodiments, it will be apparent to those of skill in the art that variations may be applied to the compositions and methods and in the steps or in the sequence of steps of the method described herein without departing from the concept, spirit, and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of any invention as defined by the appended claims.

What is claimed is:

1. A storage stable sustained release therapeutic formulation comprising:
   (a) at least one therapeutic agent, which is selected from a glucagon peptide, glucagon analog, glucagon mimetic, or salt thereof;
   (b) at least one ionization stabilizing excipient, which is a mineral acid;
   (c) at least one sustained release modifier, which is a divalent cation-donating compound; and
   (d) an aprotic polar solvent, which is dimethyl sulfoxide (DMSO),
   wherein said formulation is storage stable for at least six months at 25° C. and wherein said formulation, when administered to a patient, results in the presence of therapeutic levels of said therapeutic agent in the blood of said patient for an extended period of time relative to an immediate release formulation comprising the same therapeutic agent.

2. The formulation of claim 1, wherein the therapeutic agent is a glucagon peptide, or salt thereof.

3. The formulation of claim 1, wherein the mineral acid is selected from the group consisting of hydrochloric acid, sulfuric acid, nitric acid, and phosphoric acid.

4. The formulation of claim 1, wherein the divalent cation-donating compound contains a divalent salt of magnesium, manganese, calcium, iron, copper, aluminum, or zinc.

5. The formulation of claim 4, wherein the divalent cation-donating compound is a zinc salt.

6. The formulation of claim 5, wherein the zinc salt is selected from the group consisting of zinc acetate, zinc chloride, and zinc sulfate.

7. The formulation of claim 3, wherein the zinc salt is zinc sulfate.

8. The formulation of claim 1, wherein said formulation further comprises at least one polymer suitable for use in preparing sustained release formulations of said peptide.

9. The formulation of claim 8, wherein said polymer is a PLGA.

10. The formulation of claim 9, wherein said PLGA is an ester-terminated PLGA or an acid-terminated PLGA.

11. The formulation of claim 8, wherein said formulation provides for complete release of said peptide from said formulation into the bloodstream of an animal to which the formulation has been administered within a period of 7-14 days.

12. The formulation of claim 2, wherein the therapeutic agent is a glucagon peptide.

13. The formulation of claim 12, wherein the glucagon peptide is at a concentration of 5 mg/mL or 10 mg/mL in DMSO.

14. The formulation of claim 13, wherein the glucagon peptide is at a concentration of 5 mg/mL in DMSO.

15. The formulation of claim 13, wherein the glucagon peptide is at a concentration of 10 mg/mL in DMSO.

16. The formulation of claim 3, wherein the mineral acid is sulfuric acid or hydrochloric acid.

17. The formulation of claim 1, further comprising trehalose dihydrate.

18. The formulation of claim 17, wherein the trehalose dihydrate is at a concentration of 3.5% (w/v).

19. The formulation of claim 17, further comprising mannitol.

20. The formulation of claim 19, wherein the mannitol is at a concentration of 2.9% (w/v).

21. The formulation of claim 5, wherein the ratio of zinc:glucagon is 1:1, 2:1, 4:1, 8:1, or 16:1.

22. The formulation of claim 21, wherein the ratio of zinc:glucagon is 4:1 or 8:1.

23. A method of treating or preventing hypoglycemia by introducing an effective amount of the formulation of claim 1 into a subject in need thereof.

24. The method of claim 23, wherein the formulation is introduced into said subject via parenteral administration.

25. The method of claim 24, wherein said parenteral administration is via injection or infusion.

26. The method of claim 25, wherein said injection is a subcutaneous, intradermal or intramuscular injection.

27. The method of claim 25, wherein said infusion is intravenous.

28. The method of claim 25, wherein said infusion is accomplished by pump infusion.

29. The method of claim 28, wherein said pump infusion comprises continuous or bolus pump infusion, or a combination thereof.

30. A method of producing a storage stable sustained release therapeutic formulation, said method comprising mixing at least one ionization stabilizing excipient, which is a mineral acid, at least one sustained release modifier, which is a divalent cation-donating compound, an aprotic polar solvent, which is DMSO, and at least one therapeutic agent, which is selected from a glucagon peptide, glucagon analog, glucagon mimetic, or salt thereof, thereby forming a storage stable therapeutic formulation that, when administered to a patient, results in the presence of therapeutic levels of said therapeutic agent in the blood of said patient for an extended period of time relative to an immediate release formulation comprising the same therapeutic agent.

31. The method of claim 30, wherein the mineral acid is selected from the group consisting of hydrochloric acid, sulfuric acid, nitric acid, and phosphoric acid.

32. The method of claim 30, wherein the divalent cation-donating compound contains a divalent salt of magnesium, manganese, calcium, iron, copper, aluminum, or zinc.

33. The method of claim 32, wherein the divalent cation-donating compound is a zinc salt.

34. The method of claim 33, wherein the zinc salt is selected from the group consisting of zinc acetate, zinc chloride, and zinc sulfate.

35. The method of claim 33, wherein the zinc salt is zinc sulfate.

36. The method of claim 33, wherein the ratio of zinc:glucagon is 1:1, 2:1, 4:1, 8:1, or 16:1.

37. The method of claim 36, wherein the ratio of zinc:glucagon is 4:1 or 8:1.

38. A method of diagnosing a disease or physical disorder in a human patient by introducing an effective amount of the formulation of claim 1 into a patient suffering from or predisposed to a disease or disorder as an adjunct to a diagnostic test and conducting a diagnostic test on said patient.

39. The method of claim 38, wherein the divalent cation-donating compound contains a divalent salt of magnesium, manganese, calcium, iron, copper, aluminum, or zinc.

40. The method of claim 39, wherein the divalent cation-donating compound is a zinc salt.

41. The method of claim 40, wherein the zinc salt is selected from the group consisting of zinc acetate, zinc chloride, and zinc sulfate.

42. The method of claim 40, wherein the zinc salt is zinc sulfate.

43. The method of claim 38, wherein said patient is suffering from or predisposed to Alzheimer's Disease.

44. The method of claim 38, wherein said patient is suffering from or predisposed to a growth hormone deficiency.

45. The method of claim 38, wherein said patient is suffering from or predisposed to a gastrointestinal disorder.

46. The method of claim 38, wherein said diagnostic test is a radiology test of the gastrointestinal tract of said patient.

47. The method of claim 38, wherein said formulation is introduced into said patient intravenously, intramuscularly or intradermally.

* * * * *

UNITED STATES PATENT AND TRADEMARK OFFICE
CERTIFICATE OF CORRECTION

PATENT NO. : 11,964,003 B2
APPLICATION NO. : 17/359202
DATED : April 23, 2024
INVENTOR(S) : Cassavaugh et al.

It is certified that error appears in the above-identified patent and that said Letters Patent is hereby corrected as shown below:

In the Claims

Column 38, in Claim 18, Line 2, delete "3.5%" and insert -- 5.5% --.

Signed and Sealed this
Fourth Day of June, 2024

Katherine Kelly Vidal
*Director of the United States Patent and Trademark Office*